(12) United States Patent
Matsunami et al.

(10) Patent No.: US 8,512,965 B2
(45) Date of Patent: Aug. 20, 2013

(54) METHODS OF IDENTIFYING LIGANDS TO SOUR-TASTE RECEPTORS COMPRISING PKD1L3 AND PKDPKD2L1

(75) Inventors: Hiroaki Matsunami, Durham, NC (US); Momoka Matsunami, Durham, NC (US); Yoshiro Ishimaru, Fuchu (JP)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/590,800

(22) Filed: Aug. 21, 2012

(65) Prior Publication Data

US 2012/0322084 A1 Dec. 20, 2012

Related U.S. Application Data

(63) Continuation of application No. 13/214,830, filed on Aug. 22, 2011, now abandoned, which is a continuation of application No. 12/632,299, filed on Dec. 7, 2009, now Pat. No. 8,003,384, which is a continuation of application No. 11/825,941, filed on Jul. 10, 2007, now Pat. No. 7,629,134.

(60) Provisional application No. 60/819,675, filed on Jul. 10, 2006.

(51) Int. Cl.
*G01N 33/53* (2006.01)
*G01N 33/567* (2006.01)
*C07K 1/00* (2006.01)
*C07K 14/00* (2006.01)
*C07K 17/00* (2006.01)

(52) U.S. Cl.
USPC .............................. 435/7.1; 435/7.2; 530/350

(58) Field of Classification Search
None
See application file for complete search history.

(56) References Cited

U.S. PATENT DOCUMENTS

| | | |
|---|---|---|
| 6,608,176 B2 | 8/2003 | Chaudhari |
| 6,955,887 B2 | 10/2005 | Adler et al. ............... 435/7.2 |
| 7,223,551 B2 | 5/2007 | Adler |
| 7,297,543 B2 | 11/2007 | Zoller |
| 7,309,577 B2 | 12/2007 | Zoller |
| 7,344,859 B2 | 3/2008 | Zoller |
| 7,364,867 B2 | 4/2008 | Margolskee |
| 7,364,903 B2 | 4/2008 | Zoller |
| 7,399,601 B2 | 7/2008 | Adler |
| 7,407,769 B2 * | 8/2008 | Zuker et al. ............... 435/7.2 |
| 2002/0164645 A1 | 11/2002 | Zuker |
| 2004/0132134 A1 | 7/2004 | Adler |
| 2004/0171042 A1 | 9/2004 | Adler |
| 2004/0209286 A1 | 10/2004 | Adler |
| 2004/0248123 A1 | 12/2004 | Drayna |
| 2005/0287517 A1 | 12/2005 | Adler |
| 2006/0019346 A1 | 1/2006 | Xu |
| 2009/0089888 A1 | 4/2009 | Zuker et al. ............... 800/3 |

OTHER PUBLICATIONS

Caicedo, A., et al., "Individual Mouse Taste Cells Respond to Multiple Chemical Stimuli," Journal of Physiology (2002), 544, pp. 501-509.
Drayna, D., (2005) "Human Taste Genetics", Annu Rev Genomics Hum Genet; 6:217-35.
Hoon, J., et al., "Putative Mammalian Taste Receptors: A Class of Taste-Specific GPCRs with Distinct Topographic Selectivity", Cell 96, 541-551 (1999).
Kim, U.K., et al., "Genetics of Human Taste Perception," (2004), J. Dent. Res. 83(6), 448-453.
Murakami, M., et al., Genomic Organization and Functional Analysis of Murine PKD2L1. (2005) J. Biol. Chem. 280, 5626-5635.
Saito, Harumi, et al., "RTP Family Members Induce Functional Expression of Mammalian Odorant Receptors," (2004), Cell, 119, 679-691.
Sugita, Makoto and Yoshiki Shiba, "Genetic Tracing Shows Segregation of Taste Neuronal Circuitries for Bitter and Sweet," Science, vol. 309, Jul. 29, 2005, pp. 781-785.
Ugawa et al., 2003, "Amiloride-Insensitive Currents of the Acid-Sensing Ion Channel-2a(ASIC2a)/ASIC2b Heteromeric Sour-Taste Receptor Channel," J. Neurosci. 23:3616-3622.
Wong et al., 2002, "A p75NTR and Nogo receptor complex mediates repulsive signaling by myelin-associated glycoprotein," Nat. Neurosci. 5:1302-1308.
Yuasa et al., 2002, "The Sequence, Expression, and Chromosomal Localization of a Novel Polycystic Kidney Disease 1-Like Gene, PKD1L1, in Human," Genomics 79:376-386.
Zhang et al., 2003, "Coding of Sweet, Bitter, and Umami Tastes: Different Receptor Cells Sharing Similar Signaling Pathways," Cell 112:293-301.
Zhao et al., 2003, "The Receptors for Mammalian Sweet and Umami Taste," Cell 115:255-266.
Adler et al., 2000, "A Novel Family of Mammalian Taste Receptors," Cell 100:693-702.
Barr and Sternberg, "A polycystic kidney-disease gene homologue required for male mating behavior in *C. elegans*," 1999, Nature 401:386-389.
Barr et al., 2001, "The *Caenorhabditis elegans* autosomal dominant polycystic kidney disease gene homologs lov-1 and pkd-2 act in the same pathway," Curr. Biol. 11:1341-1346.
Behrens, et al., "Members of RTP and REEP Gene Families Influence Functional Bitter Taste Receptor Expression," The Journal of Biological Chemistry, vol. 281, No. 29, pp. 20650-20659, Jul. 21, 2006.
Chandrashekar et al., 2000, "T2Rs Function as Bitter Taste Receptors," Cell 100:703-711.

(Continued)

*Primary Examiner* — Robert Landsman
(74) *Attorney, Agent, or Firm* — Casimir Jones SC

(57) ABSTRACT

The present invention relates to sour taste receptors and compositions and methods thereof. In particular, the present invention provides assays and methods of screening for ligands specific for sour taste receptors. Additionally, the present invention provides methods for screening for accessory proteins and mutations, polymorphisms and other potential sour taste receptor protein mutations that are associated with disease states, and therapeutic agents, ligands, and modulators of such proteins. The present invention also provides compositions and methods for modulating sour taste receptors in vitro and in vivo.

9 Claims, 2 Drawing Sheets

(56) References Cited

OTHER PUBLICATIONS

Chen et al., 1999, "Polycystin-L is a calcium-regulated cation channel permeable to calcium ions," Nature 401:386-386.
Clapham, 2003, "TRP channels as cellular sensors," Nature 426:517-524.
Clapp et al., 2001, "Immunocytochemical evidence for co-expression of Type III IP3 receptor with signaling components of bitter taste transduction," Neurosci. 2:6.
Corey et al., 2004, "TRPA1 is a candidate for the mechanosensitive transduction channel of vertebrate hair cells," Nature 432:723-730.
Damak et al., 2003, "Detection of Sweet and Umami Taste in the Absence of Taste Receptor T1r3," Science 301:850-853.
Delmas et al., 2004, "Polycystins, calcium signaling, and human diseases," Biochem. Biophys. Res. Commun. 322:1374-1383.
Faus, 2000, "Recent developments in the characterization and biotechnological production of sweet-tasting proteins," Appl. Microbiol. Biotechnol. 53:145-151.
Ganzevles and Kroeze, 1987, "Effects of Adaptation and Cross-Adaptation to Common Ions on Sourness Intensity," Physiol. Behav. 40:641-646.
Gonzalez-Perrett et al., 2001, "Polycystin-2, the protein mutated in autosomal dominant polycystic kidney disease (ADPKD), is a Ca2+-permeable nonselective cation channel," Proc. Natl. Acad. Sci. 98:1182-1187.
Guo et al., 2000, "Identification and Characterization of a Novel Polycystin Family Member . . . ", Genomics 241-251.
Hanaoka et al., "Co-assembly of polycystin-1 and -2 produces unique cation-permeable currents," 2000, Nature 408:990-994.
Hughes et al., 1999, "Identification of a human homologue of the sea urchin receptor for egg jelly: a polycystic kidney disease-like protein," Hum. Mol. Genet. 8:543-549.
International Search Report and Written Opinion from PCT/US2007/15288, Apr. 9, 2008.
Ishimaru, et al., "Transient receptor potential family members PKD1L3 and PKD2L1 form a candidate sour taste receptor," PNAS, Aug. 15, 2006, vol. 103, No. 33, pp. 12569-12574.
Kitagawa et al., 2001, "Molecular Genetic Identification of a Candidate Receptor Gene for Sweet Taste," Biochem. Biophys. Res. Comm. 283:236-242.
Kohmura et al., 2002, "Structure-taste relationships of the sweet protein monellin," Pure Appl. Chem. 74:1235-1242.
Jones, "Golf: An Olfactory Neuron Specific-G Protein Involved in Odorant Siognal Transduction," Science, May 19, 1989, vol. 244, pp. 790-795.
Li et al., 2002, "Human receptors for sweet and umami taste," Proc. Natl. Acad. Sci. 99:4692-4693.
Li et al., 2003, "Identification of two novel polycystic kidney disease-1-like genes in human and mouse genomes," Genomics 81:596-608.
Lindemann et al., 1996, "Taste Reception," Physiol. Rev. 76:718-66.
Lingueglia et al., 1997, "A Modulatory Subunit of Acid Sensing Ion Channels in Brain and Dorsal Root Ganglion Cells," J. Biol. Chem. 272:29778-29783.
Lopezjimenez, N.D., et al., "Two members of the TRPP family of ion channels, Pkd1l3 and Pkd2l11, are co-expressed in a subset of taste receptor cells," J. Neurochemistry. Jul. 2006, vol. 98, pp. 68-77.
Ludwig et al., 1998, "A family of hyperpolarization-activated mammalian cation channels," Nature 393:587-691.
Makhlouf and Blum, 1972, "Kinetics of the Taste Response to Chemical Stimulation: A Theory of Acid Taste in Man," Gastroenterology 63:67-75.
Margolskee, 2002, "Molecular Mechanisms of Bitter and Sweet Taste Transduction," J. Biol. Chem. 277:1-4.
Matsunami et al., 2000, "A family of candidate taste receptors in human and mouse," Nature 404:601-604.
Max et al., 2001, "Tas1r3, encoding a new candidate taste receptor, is allelic to the sweet responsiveness locus Sac," Nat Genet. 28:58-63.
Miyamoto et al., 2000, "Acid and salt responses in mouse taste cells," Prog. Neurobiol. 62:135-157.
Miyoshi et al., 2001, "IP3 receptor type 3 and PLCβ2 are co-expressed with taste receptors T1R and T2R in rat taste bud cells," Chem Senses 26:259-265.
Montell, 2005 Sci. STKE (Feb. 22, 2005), "The TRP Superfamily of Cation Channels,".
Montmayeur and Matsunami, 2002, "Receptors for bitter and sweet taste," Curr Opin. Neurobiol. 12:366-371.
Montmayeur et al., 2001, "A candidate taste receptor gene near a sweet taste locus," Nat. Neurosci 4:492-498.
Moosmang et al., 1999, "Differential Distribution of Four Hyperpolarization-Activated Cation Channels in Mouse Brain," Biol. Chem. 380:975-980.
Mueller et al., 2005, "The receptors and coding logic for bitter taste," Nature 434:225-229.
Nauli and Zhou, 2004, "Polycystins and mechanosensation in renal and nodal cilia," Bioessays 26:844-856.
Nauli et al., 2003, "Polycystins 1 and 2 mediate mechanosensation in the primary cilium of kidney cells," Nat Genet. 33:129-137.
Nelson et al., 2001, "Mammalian Sweet Taste Receptors," Cell 106:381-390.
Nelson et al., 2002, "An amino-acid taste receptor," Nature 416:199-202.
Nomura et al., 1998, "Identification of PKDL, a Novel Polycystic Kidney Disease 2-Like Gene Whose Murine Homologue is Deleted in Mice with Kidney and Retinal Defects," J. Biol. Chem. 273:25967-25973.
Perez et al., 2002, "A transient receptor potential channel expressed in taste receptor cells," Nat. Neurosci. 5:1169-1176.
Richter, T.A., et al., "Sour taste stimuli evoke Ca2+ and pH responses in mouse taste cells," J. Physiol (2003) 547:2, pp. 475-483.
Richter et al., 2004, "Acid-Sensing Ion Channel-2 is Not Necessary for Sour Taste in Mice," J. Neurosci. 24:4088-4091.
Scott, 2004, "The Sweet and the Bitter of Mammalian Taste," Curr. Opin Neurobiol. 14:423-427.
Stevens et al., 2001, "Hyperpolarization-activated channels HCN1 and HCN4 mediate responses to sour stimuli," Nature 413:631-635.
Ugawa et al., "Receptor that leaves a sour taste in the mouth," 1998, Nature 395:555-556.
Ugawa S. Anatomical Science International 78:205-210, 2003.

\* cited by examiner

Sweet Receptor: T1R2+T1R3
Umami Receptor: T1R1+T1R3
Sour Receptor: PKD1L3+PKD2L1

SEQUENCE LISTING

```
<160> NUMBER OF SEQ ID NOS: 8

<210> SEQ ID NO 1
<211> LENGTH: 6456
<212> TYPE: DNA
<213> ORGANISM: Mus musculus

<400> SEQUENCE: 1
atgctcttgc agaggcggtc ctggctctgg ctgtacatta gaatcggtgt cattctgggt      60
gatattttgg gacgtaaacc aagcatccgg gagcaacatg ggggaaacag ctgctatcag     120
cttaacagac tttctgtga cttccaggaa gcagataact actgccacgc ccagagagga     180
cgcctagccc acacgtggaa ccccaagctt cggggtttcc taaaaagctt cctgaatgaa     240
gaaacagtgt ggtgggtcag gggaaacctg acgctgcccg gatcgcatcc agggataaat     300
cagacaggag gtgatgacgt cttaaggaac caaaagcctg gcgagtgccc ttccgtggtc     360
```

```
acacactcta atgctgtctt ctcaagatgg aacctgtgca tagagaagca tcatttcatt    420
tgccaggctg ccgcctttcc ccctcaaggt gcaagcattt ggagaaatga gtttggtcct    480
ggtcctctgt tacccatgaa aagaagagga gctgagacag agagacatat gatcccagga    540
aatggccccc cgttagccat gtgtcaccaa cccgctcctc ctgagctttt tgagacattg    600
tgctttccca ttgacccagc ttcttcagca cctccaaaag ccacacacag gatgacaatc    660
acatccctaa ctggaaggcc acaggtgaca tcagacacac ttgcatccag cagcccacca    720
caggggacat cagacacacc tgcatccagc agcccaccac aggtgacatc agccacatct    780
gcatctagca gcccaccaca ggggacatca gacacacctg catccagcag cccaccacag    840
gtgacatcag ccacatctgc atctagcagc ccaccacagg ggacatcaga cacacctgca    900
tccagcagcc caccacaggt gacatcagcc acatctgcat ctagcagccc accacagggg    960
acatcagaca cacctgcatc cagcagccca ccacaggtga catcagccac atctgcatct   1020
agcagcccac cacaggggac atcagacaca cctgcatcca gcagcccacc aggggacatt   1080
ttagacacac cttcatctag cagcccacca ggggacatca gacacacctg catccagc    1140 agcccaccac aggggacatc agagacacct gcatccaaca gcccaccaca ggggacatca   1200
gagacacctg gattcagcag cccaccacag gtgacaacag ccacacttgt atccagcagc   1260
ccaccacagg tgacatcaga gacacctgca tccagcagcc caacacaggt gacatcagag   1320
acacctgcat ccagcagccc aacacaggtg acatcagaca cacctgcatc caatagccca   1380
ccacagggga catcagacac acctggattc agcagcccaa cacaggtgac aacagccaca   1440
cttgtatcca gcagcccacc acaggtgaca tcagacacac ctgcatccag cagcccacca   1500
caggtgacat cagacacacc tgcatccagc agcccaccac aggtgacatc agagacacct   1560
gcatccagca gcccaccaca ggtgacatca gacacatctg catccatcag cccaccacag   1620
gtaatatcag acacacctgc atccagcagc ccaccacagg tgacatcaga gacacctgca   1680
tccagcagcc caacaaacat gacatcagac acacctgcat ccagcagccc aacaaacatg   1740
acatcagaca cacctgcatc cagcagccca acaaacatga catcagacac acctgcatcc   1800
agcagcccac catggcctgt tataacagag gtcaccaggc ctgaatccac aatacctgct   1860
ggaagatctt tggcaaacat cacttcaaag gcacaggaag actctcccct gggagtcatc   1920
tctacccatc cacagatgtc atttcagagt tcaaccagtc aggccttgga tgagacagca   1980
ggggaacggg tcccaacaat tcctgatttc caagcccaca gtgaattcca gaaagcttgt   2040
gccatcctcc agagactgag agacttcctg ccgacttctc ccacatcagc tcaggtcagt   2100
gtggccaatt tactcattga cctgagtgag cagttgctgg tgctcccgtt tcagaagaac   2160
aacagttgga gctctcaaac tccagcagtc agctgcccct tccagcctct tggacgtcta   2220
acaacaacgg aaaaaagcag tcatcagatg gctcagcaag acatggaaca ggttgaagac   2280
atgctggaga catccctgat ggccctgggg gagatccaca gagcattttg ccagcagagt   2340
ctgtgccctc agtcagcagt gaccctggcc tctccctctg ctactctgat gttgagcagc   2400
caaaatgtgt caacgttgcc cctgagcacc tacactttgg gtgagcctgc acccttgact   2460
ttgggcttcc cgtcagcaga agctctgaag gagctcttga acaaacaccc aggcgtgaac   2520
cttcaagtga caggtctggc tttcaaccct tttaagactt tggatgacaa gaacattgtt   2580
ggaagcattg gaaatgtgca gctgagctct gcttatcagt cgatcagagt ccacgactta   2640
atagaagata ttgagatcat gctctggaga aatgccagca tggagaccca gcccaccagc   2700
ctcaacacaa gtacagacca tttcacaatc tctgtgaaca tcacttcctt ggagaagacc   2760
```

```
ctcattgtga ccatcgagcc tgaaagtccc ctcctaatga cgctccactt gggcttccag    2820
gaccagctgg cccacactca cttctatctc aacatcagcc tgccaaggga ccaagtgtgg    2880
cagaaagatg aggagtacac gtgggtgctg acaccagaga acctgtggta cgggactggc    2940
acctactaca taatggctgt ggagaataaa agtacagagg cggcacagca cacacccgtc    3000
ctggtctcag tggtcacagc tgtcacccag tgctatttct gggaccgata caataggaca    3060
tggaagagcg atggatgcca agtggggccg aagagcacca ttttaaagac acagtgtctc    3120
tgtgaccacc tgaccttctt cagcagcgac ttcttcagcg tgccgaggac ggtggatgta    3180
gaaaacacca tcaaactgct tcttcatgtg accaacaacc ctgtcggggt gtcattgctg    3240
tccagcctcc taggattcta tatcctctta gccatgtggg cttccagaaa ggatcgagaa    3300
gatatgcaga aggtgaaggt aacagtcctg gctgacaatg accccagctc tgcatcccac    3360
taccttatcc aggtctacac tggctatcgg aggagggctg ctaccaccgc caaggtcgtt    3420
atcactctct atggctcaga ggggcacagt gagccccacc acctttgtga ccctgagaag    3480 acagttttg agcgtggagc actggatgtt ttccttcttt ccaccggatc ctggctgggg    3540
gacctgcatg gccttcggct gtggcatgac aattctggcg acagcccttc ttggtatgta    3600
agccaggtga tcgtcagtga catgaccacg aggaagaaat ggcatttcca gtgcaattgt    3660
tggctggccg tggacttggg caactgtgag cgtgacaggg tgttcacacc agcctccaga    3720
agcgagctct cttccttcag acacctgttc tcctccacaa tcgtagaaaa gttcacccag    3780
gattatctgt ggctctcagt tgcaactcga catccctgga accagtttac acgagtccag    3840
aggctctcct gctgcatggc actactgctc tgtgacatgg tcatcaatat tatgttctgg    3900
aagatgggtg gcaccactgc caagagggc accgaacaac taggtccact tgctgtgacc    3960
ttgtcggagc tgctcgtcag catccagacc tccatcatcc tcttccccat ccacctcatc    4020
tttgggcggc tcttccagtt gattcaccca ccagaagctc tgcccagct tccttcatc    4080 caggctgcct ggcccctgc tcttgtttgt gagtcccct ctcttacaca ggtggtcaag    4140
gaattaaagg aaactgtggg attcctgctc aggagaaata cacagctgct ctcggagtgt    4200
gagccgtctt cgtgcagttc ttgtgacatt aacaagctgg cgaagctttt atccggcctc    4260
atttactgtc acttagaaga cgaaggctgt caccagcaga cagaatccca ctgggaagac    4320
gcagtgtctg aaaaccatta ccatttctgc cgctaccttc tccaacttct gcggagactg    4380
aaagcgcatt tagaggctct tggtgctacc caggatcacc agtcttgtga tttctcagaa    4440
gcagtcagcc aacttcaaaa cctccaggaa ctcctggaga cacagactct ccgcagaggg    4500
ccagggccat gcaggcattc caccagtttc cccatcctca gcccaggaga agggaagaag    4560
cccatgtcat tttgcctgtt cagatggttg aagtgcagct gctggctcct tcttggtgtc    4620
atcagcctgg cctcggcctt ttttataacg ctctatagct tggagttgga caaagaccaa    4680
gccaccagct gggttatttc aatgatgctg tcggtactac aagacatctt tatcagccag    4740
ccgataaagg tcatcttcct gacattgttg ttctccctga tggcaaacca catgccgtgg    4800
cttaacaaag acaaggaaca cacgcccgg agaatcgtag cactttgggc aaagtgtcct    4860
tggtcggcac ctggcttgag agacaagaac aatcccatct acactgcccc agcaatgaac    4920
aacctagcca agcctacaag gaaggcctgg aagaagcagc tctccaagct gacgggtggt    4980
actctggtgc aaatcctctt cctgaccctg ctgatgacta ccgtctattc tgcaaaggac    5040
tctagtcgat ttttcctcca tcgagctatc tggaagaggt tttctcaccg tttctcagaa    5100
atcaaaactg tagaggattt ctaccccctgg gccaacggca ccctccttcc taacctatat    5160
```

```
ggggattaca gaggatttat tactgacggg aactcctttc ttctgggcaa tgttttgatc    5220
cgccagactc gcattcctaa tgacatattc ttcccaggat ctctccacaa gcaaatgaag    5280
tcgcctcccc aacatcagga ggacagagag aactatgggg ctggctgggt ccccccctgac   5340 acaaacatca caaaagtaga cagtatttgg cattatcaga atcaggagtc gctgggaggc    5400
tatcccatcc aagggagct agccacttac tcaggaggag ctatgttgt gaggcttgga     5460 agaaaccaca gtgcggcaac cagggttctg cagcatctgg aacagaggcg ctggctggac    5520
cactgcacaa aagcccctctt tgtagaattc acggtcttca atgctaatgt gaatctgctc    5580
tgtgcggtga ccctcatctt ggaatccagt ggtgtgggga cttttcctcac ctcccctgcaa   5640 ctggacagtt taacttccct tcagtcatca gagaggggct cgcctggat cgtctcacag      5700 gtcgtctact accttctcgt ctgttactat gccttcatcc agggctgtcg gctgaagcgg     5760
cagaggctgg cgttcttcac taggaaaagg aacctcctgg acacaagcat cgtcctcatt    5820
agcttcagca tcctgggcct cagcatgcag agcctctctc tacttcacaa aaagatgcag    5880
cagtaccact gtgaccggga caggttcatc agtttctacg aggcactgag agtgaactct    5940
gcagtcaccc acctcagggg cttcctgctt ctcttcgcaa ctgtgcgggt ctgggaccta    6000
ctgcgacatc atgcccagtt acaggtcatc aacaagacac tgtccaaagc ctgggacgag    6060
gtgctgggct ttatactgat catcgtggtc ctgttaagca gctatgccat gactttcaac    6120
ctgctgtttg gatggagcat ctctgactac cagagcttct tcagatctat agtgactgtt    6180
gttggcctct tgatgggaac ttcaaagcac aaggaggtta ttgctctata cccaatcctg    6240
ggctcccttt tggttctcag tagcatcatc ttgatgggac ttgtgatcat taatcttttt    6300
gtttctgcca ttctcattgc ctttgggaaa gaaaggaagg cctgtgagaa agaagctaca    6360
ctgacagata tgttactaca aaagctctca agtctgttag gaatccgcct gcaccagaat    6420
ccatctgagg aacacgctga caacactggg tattga                              6456
```

<210> SEQ ID NO 2
<211> LENGTH: 2151
<212> TYPE: PRT
<213> ORGANISM: Mus musculus

<400> SEQUENCE: 2

```
Met Leu Leu Gln Arg Arg Ser Trp Leu Trp Leu Tyr Ile Arg Ile Gly
 1               5                  10                  15

Val Ile Leu Gly Asp Ile Leu Gly Arg Lys Pro Ser Ile Arg Glu Gln
            20                  25                  30

His Gly Gly Asn Ser Cys Tyr Gln Leu Asn Arg Leu Phe Cys Asp Phe
        35                  40                  45

Gln Glu Ala Asp Asn Tyr Cys His Ala Gln Arg Gly Arg Leu Ala His
    50                  55                  60

Thr Trp Asn Pro Lys Leu Arg Gly Phe Leu Lys Ser Phe Leu Asn Glu
65                  70                  75                  80

Glu Thr Val Trp Trp Val Arg Gly Asn Leu Thr Leu Pro Gly Ser His
                85                  90                  95

Pro Gly Ile Asn Gln Thr Gly Gly Asp Asp Val Leu Arg Asn Gln Lys
            100                 105                 110

Pro Gly Glu Cys Pro Ser Val Val Thr His Ser Asn Ala Val Phe Ser
        115                 120                 125

Arg Trp Asn Leu Cys Ile Glu Lys His His Phe Ile Cys Gln Ala Ala
    130                 135                 140
```

-continued

```
Ala Phe Pro Pro Gln Gly Ala Ser Ile Trp Arg Asn Glu Phe Gly Pro
145                 150                 155                 160

Gly Pro Leu Leu Pro Met Lys Arg Arg Gly Ala Glu Thr Glu Arg His
                165                 170                 175

Met Ile Pro Gly Asn Gly Pro Pro Leu Ala Met Cys His Gln Pro Ala
            180                 185                 190

Pro Pro Glu Leu Phe Glu Thr Leu Cys Phe Pro Ile Asp Pro Ala Ser
        195                 200                 205

Ser Ala Pro Pro Lys Ala Thr His Arg Met Thr Ile Thr Ser Leu Thr
    210                 215                 220

Gly Arg Pro Gln Val Thr Ser Asp Thr Leu Ala Ser Ser Ser Pro Pro
225                 230                 235                 240

Gln Gly Thr Ser Asp Thr Pro Ala Ser Ser Pro Pro Gln Val Thr
                245                 250                 255

Ser Ala Thr Ser Ala Ser Ser Pro Pro Gln Gly Thr Ser Asp Thr
                260                 265                 270

Pro Ala Ser Ser Pro Pro Gln Val Thr Ser Ala Thr Ser Ala Ser
    275                 280                 285

Ser Ser Pro Pro Gln Gly Thr Ser Asp Thr Pro Ala Ser Ser Ser Pro
    290                 295                 300

Pro Gln Val Thr Ser Ala Thr Ser Ala Ser Ser Pro Pro Gln Gly
305                 310                 315                 320

Thr Ser Asp Thr Pro Ala Ser Ser Pro Pro Gln Val Thr Ser Ala
                325                 330                 335

Thr Ser Ala Ser Ser Ser Pro Pro Gln Gly Thr Ser Asp Thr Pro Ala
                340                 345                 350

Ser Ser Ser Pro Pro Gln Gly Thr Leu Asp Thr Pro Ser Ser Ser
            355                 360                 365

Pro Pro Gln Gly Thr Ser Asp Thr Pro Ala Ser Ser Pro Pro Gln
        370                 375                 380

Gly Thr Ser Glu Thr Pro Ala Ser Asn Ser Pro Gln Gly Thr Ser
385                 390                 395                 400

Glu Thr Pro Gly Phe Ser Ser Pro Pro Gln Val Thr Thr Ala Thr Leu
                405                 410                 415

Val Ser Ser Ser Pro Pro Gln Val Thr Ser Glu Thr Pro Ala Ser Ser
                420                 425                 430

Ser Pro Thr Gln Val Thr Ser Glu Thr Pro Ala Ser Ser Ser Pro Thr
        435                 440                 445

Gln Val Thr Ser Asp Thr Pro Ala Ser Asn Ser Pro Gln Gly Thr
    450                 455                 460

Ser Asp Thr Pro Gly Phe Ser Ser Pro Thr Gln Val Thr Thr Ala Thr
465                 470                 475                 480

Leu Val Ser Ser Ser Pro Pro Gln Val Thr Asp Thr Pro Ala Ser
                485                 490                 495

Ser Ser Pro Pro Gln Val Thr Ser Asp Thr Pro Ala Ser Ser Ser Pro
        500                 505                 510

Pro Gln Val Thr Ser Glu Thr Pro Ala Ser Ser Pro Pro Gln Val
        515                 520                 525

Thr Ser Asp Thr Ser Ala Ser Ile Ser Pro Gln Val Ile Ser Asp
    530                 535                 540

Thr Pro Ala Ser Ser Ser Pro Pro Gln Val Thr Ser Glu Thr Pro Ala
545                 550                 555                 560

Ser Ser Ser Pro Thr Asn Met Thr Ser Asp Thr Pro Ala Ser Ser Ser
                565                 570                 575
```

```
Pro Thr Asn Met Thr Ser Asp Thr Pro Ala Ser Ser Pro Thr Asn
            580                 585                 590

Met Thr Ser Asp Thr Pro Ala Ser Ser Pro Pro Trp Pro Val Ile
        595                 600                 605

Thr Glu Val Thr Arg Pro Glu Ser Thr Ile Pro Ala Gly Arg Ser Leu
610                 615                 620

Ala Asn Ile Thr Ser Lys Ala Gln Glu Asp Ser Pro Leu Gly Val Ile
625                 630                 635                 640

Ser Thr His Pro Gln Met Ser Phe Gln Ser Thr Ser Gln Ala Leu
            645                 650                 655

Asp Glu Thr Ala Gly Glu Arg Val Pro Thr Ile Pro Asp Phe Gln Ala
                660                 665                 670

His Ser Glu Phe Gln Lys Ala Cys Ala Ile Leu Gln Arg Leu Arg Asp
            675                 680                 685

Phe Leu Pro Thr Ser Pro Thr Ser Ala Gln Val Ser Val Ala Asn Leu
    690                 695                 700

Leu Ile Asp Leu Ser Glu Gln Leu Leu Val Leu Pro Phe Gln Lys Asn
705                 710                 715                 720

Asn Ser Trp Ser Ser Gln Thr Pro Ala Val Ser Cys Pro Phe Gln Pro
                725                 730                 735

Leu Gly Arg Leu Thr Thr Thr Glu Lys Ser Ser His Gln Met Ala Gln
                740                 745                 750

Gln Asp Met Glu Gln Val Glu Asp Met Leu Glu Thr Ser Leu Met Ala
            755                 760                 765

Leu Gly Glu Ile His Arg Ala Phe Cys Gln Gln Ser Leu Cys Pro Gln
770                 775                 780

Ser Ala Val Thr Leu Ala Ser Pro Ser Ala Thr Leu Met Leu Ser Ser
785                 790                 795                 800

Gln Asn Val Ser Thr Leu Pro Leu Ser Thr Tyr Thr Leu Gly Glu Pro
                805                 810                 815

Ala Pro Leu Thr Leu Gly Phe Pro Ser Ala Glu Ala Leu Lys Glu Leu
                820                 825                 830

Leu Asn Lys His Pro Gly Val Asn Leu Gln Val Thr Gly Leu Ala Phe
            835                 840                 845

Asn Pro Phe Lys Thr Leu Asp Asp Lys Asn Ile Val Gly Ser Ile Gly
            850                 855                 860

Asn Val Gln Leu Ser Ser Ala Tyr Gln Ser Ile Arg Val His Asp Leu
865                 870                 875                 880

Ile Glu Asp Ile Glu Ile Met Leu Trp Arg Asn Ala Ser Met Glu Thr
                885                 890                 895

Gln Pro Thr Ser Leu Asn Thr Ser Thr Asp His Phe Thr Ile Ser Val
            900                 905                 910

Asn Ile Thr Ser Leu Glu Lys Thr Leu Ile Val Thr Ile Glu Pro Glu
            915                 920                 925

Ser Pro Leu Leu Met Thr Leu His Leu Gly Phe Gln Asp Gln Leu Ala
            930                 935                 940

His Thr His Phe Tyr Leu Asn Ile Ser Leu Pro Arg Asp Gln Val Trp
945                 950                 955                 960

Gln Lys Asp Glu Glu Tyr Thr Trp Val Leu Thr Pro Glu Asn Leu Trp
                965                 970                 975

Tyr Gly Thr Gly Thr Tyr Tyr Ile Met Ala Val Glu Asn Lys Ser Thr
                980                 985                 990

Glu Ala Ala Gln His Thr Pro Val  Leu Val Ser Val Val  Thr Ala Val
```

```
              995                 1000                1005
    Thr  Gln  Cys  Tyr  Phe  Trp  Asp  Arg  Tyr  Asn  Arg  Thr  Trp  Lys  Ser
         1010                1015                1020

Asp  Gly  Cys  Gln  Val  Gly  Pro  Lys  Ser  Thr  Ile  Leu  Lys  Thr  Gln
         1025                1030                1035

Cys  Leu  Cys  Asp  His  Leu  Thr  Phe  Phe  Ser  Ser  Asp  Phe  Phe  Ser
         1040                1045                1050

Val  Pro  Arg  Thr  Val  Asp  Val  Glu  Asn  Thr  Ile  Lys  Leu  Leu  Leu
         1055                1060                1065

His  Val  Thr  Asn  Asn  Pro  Val  Gly  Val  Ser  Leu  Leu  Ser  Ser  Leu
         1070                1075                1080

Leu  Gly  Phe  Tyr  Ile  Leu  Leu  Ala  Met  Trp  Ala  Ser  Arg  Lys  Asp
         1085                1090                1095

Arg  Glu  Asp  Met  Gln  Lys  Val  Lys  Val  Thr  Val  Leu  Ala  Asp  Asn
         1100                1105                1110

Asp  Pro  Ser  Ser  Ala  Ser  His  Tyr  Leu  Ile  Gln  Val  Tyr  Thr  Gly
         1115                1120                1125

Tyr  Arg  Arg  Arg  Ala  Ala  Thr  Thr  Ala  Lys  Val  Val  Ile  Thr  Leu
         1130                1135                1140

Tyr  Gly  Ser  Glu  Gly  His  Ser  Glu  Pro  His  His  Leu  Cys  Asp  Pro
         1145                1150                1155

Glu  Lys  Thr  Val  Phe  Glu  Arg  Gly  Ala  Leu  Asp  Val  Phe  Leu  Leu
         1160                1165                1170

Ser  Thr  Gly  Ser  Trp  Leu  Gly  Asp  Leu  His  Gly  Leu  Arg  Leu  Trp
         1175                1180                1185

His  Asp  Asn  Ser  Gly  Asp  Ser  Pro  Ser  Trp  Tyr  Val  Ser  Gln  Val
         1190                1195                1200

Ile  Val  Ser  Asp  Met  Thr  Thr  Arg  Lys  Lys  Trp  His  Phe  Gln  Cys
         1205                1210                1215

Asn  Cys  Trp  Leu  Ala  Val  Asp  Leu  Gly  Asn  Cys  Glu  Arg  Asp  Arg
         1220                1225                1230

Val  Phe  Thr  Pro  Ala  Ser  Arg  Ser  Glu  Leu  Ser  Ser  Phe  Arg  His
         1235                1240                1245

Leu  Phe  Ser  Ser  Thr  Ile  Val  Glu  Lys  Phe  Thr  Gln  Asp  Tyr  Leu
         1250                1255                1260

Trp  Leu  Ser  Val  Ala  Thr  Arg  His  Pro  Trp  Asn  Gln  Phe  Thr  Arg
         1265                1270                1275

Val  Gln  Arg  Leu  Ser  Cys  Cys  Met  Ala  Leu  Leu  Leu  Cys  Asp  Met
         1280                1285                1290

Val  Ile  Asn  Ile  Met  Phe  Trp  Lys  Met  Gly  Gly  Thr  Thr  Ala  Lys
         1295                1300                1305

Arg  Gly  Thr  Glu  Gln  Leu  Gly  Pro  Leu  Ala  Val  Thr  Leu  Ser  Glu
         1310                1315                1320

Leu  Leu  Val  Ser  Ile  Gln  Thr  Ser  Ile  Ile  Leu  Phe  Pro  Ile  His
         1325                1330                1335

Leu  Ile  Phe  Gly  Arg  Leu  Phe  Gln  Leu  Ile  His  Pro  Pro  Glu  Ala
         1340                1345                1350

Leu  Pro  Gln  Leu  Pro  Phe  Ile  Gln  Ala  Ala  Trp  Pro  Pro  Ala  Leu
         1355                1360                1365

Val  Cys  Glu  Ser  Pro  Ser  Leu  Thr  Gln  Val  Val  Lys  Glu  Leu  Lys
         1370                1375                1380

Glu  Thr  Val  Gly  Phe  Leu  Leu  Arg  Arg  Asn  Thr  Gln  Leu  Leu  Ser
         1385                1390                1395
```

```
Glu Cys Glu Pro Ser Ser Cys Ser Ser Cys Asp Ile Asn Lys Leu
1400                1405                1410

Ala Lys Leu Leu Ser Gly Leu Ile Tyr Cys His Leu Glu Asp Glu
1415                1420                1425

Gly Cys His Gln Gln Thr Glu Ser His Trp Glu Asp Ala Val Ser
1430                1435                1440

Glu Asn His Tyr His Phe Cys Arg Tyr Leu Leu Gln Leu Leu Arg
1445                1450                1455

Arg Leu Lys Ala His Leu Glu Ala Leu Gly Ala Thr Gln Asp His
1460                1465                1470

Gln Ser Cys Asp Phe Ser Glu Ala Val Ser Gln Leu Gln Asn Leu
1475                1480                1485

Gln Glu Leu Leu Glu Thr Gln Thr Leu Arg Arg Gly Pro Gly Pro
1490                1495                1500

Cys Arg His Ser Thr Ser Phe Pro Ile Leu Ser Pro Gly Glu Gly
1505                1510                1515

Lys Lys Pro Met Ser Phe Cys Leu Phe Arg Trp Leu Lys Cys Ser
1520                1525                1530

Cys Trp Leu Leu Leu Gly Val Ile Ser Leu Ala Ser Ala Phe Phe
1535                1540                1545

Ile Thr Leu Tyr Ser Leu Glu Leu Asp Lys Asp Gln Ala Thr Ser
1550                1555                1560

Trp Val Ile Ser Met Met Leu Ser Val Leu Gln Asp Ile Phe Ile
1565                1570                1575

Ser Gln Pro Ile Lys Val Ile Phe Leu Thr Leu Leu Phe Ser Leu
1580                1585                1590

Met Ala Asn His Met Pro Trp Leu Asn Lys Asp Lys Glu Gln His
1595                1600                1605

Ala Arg Arg Ile Val Ala Leu Trp Ala Lys Cys Pro Trp Ser Ala
1610                1615                1620

Pro Gly Leu Arg Asp Lys Asn Asn Pro Ile Tyr Thr Ala Pro Ala
1625                1630                1635

Met Asn Asn Leu Ala Lys Pro Thr Arg Lys Ala Trp Lys Lys Gln
1640                1645                1650

Leu Ser Lys Leu Thr Gly Gly Thr Leu Val Gln Ile Leu Phe Leu
1655                1660                1665

Thr Leu Leu Met Thr Thr Val Tyr Ser Ala Lys Asp Ser Ser Arg
1670                1675                1680

Phe Phe Leu His Arg Ala Ile Trp Lys Arg Phe Ser His Arg Phe
1685                1690                1695

Ser Glu Ile Lys Thr Val Glu Asp Phe Tyr Pro Trp Ala Asn Gly
1700                1705                1710

Thr Leu Leu Pro Asn Leu Tyr Gly Asp Tyr Arg Gly Phe Ile Thr
1715                1720                1725

Asp Gly Asn Ser Phe Leu Leu Gly Asn Val Leu Ile Arg Gln Thr
1730                1735                1740

Arg Ile Pro Asn Asp Ile Phe Phe Pro Gly Ser Leu His Lys Gln
1745                1750                1755

Met Lys Ser Pro Pro Gln His Gln Glu Asp Arg Glu Asn Tyr Gly
1760                1765                1770

Ala Gly Trp Val Pro Pro Asp Thr Asn Ile Thr Lys Val Asp Ser
1775                1780                1785

Ile Trp His Tyr Gln Asn Gln Glu Ser Leu Gly Gly Tyr Pro Ile
1790                1795                1800
```

| Gln | Gly | Glu | Leu | Ala | Thr | Tyr | Ser | Gly | Gly | Tyr | Val | Val | Arg |
| --- | --- | --- | --- | --- | --- | --- | --- | --- | --- | --- | --- | --- | --- |
| | 1805 | | | | 1810 | | | | 1815 | | | | |

Gln Gly Glu Leu Ala Thr Tyr Ser Gly Gly Tyr Val Val Arg
     1805                  1810                1815

Leu Gly Arg Asn His Ser Ala Ala Thr Arg Val Leu Gln His Leu
     1820                  1825                1830

Glu Gln Arg Arg Trp Leu Asp His Cys Thr Lys Ala Leu Phe Val
     1835                  1840                1845

Glu Phe Thr Val Phe Asn Ala Asn Val Asn Leu Leu Cys Ala Val
     1850                  1855                1860

Thr Leu Ile Leu Glu Ser Ser Gly Val Gly Thr Phe Leu Thr Ser
     1865                  1870                1875

Leu Gln Leu Asp Ser Leu Thr Ser Leu Gln Ser Ser Glu Arg Gly
     1880                  1885                1890

Phe Ala Trp Ile Val Ser Gln Val Val Tyr Tyr Leu Leu Val Cys
     1895                  1900                1905

Tyr Tyr Ala Phe Ile Gln Gly Cys Arg Leu Lys Arg Gln Arg Leu
     1910                  1915                1920

Ala Phe Phe Thr Arg Lys Arg Asn Leu Leu Asp Thr Ser Ile Val
     1925                  1930                1935

Leu Ile Ser Phe Ser Ile Leu Gly Leu Ser Met Gln Ser Leu Ser
     1940                  1945                1950

Leu Leu His Lys Lys Met Gln Gln Tyr His Cys Asp Arg Asp Arg
     1955                  1960                1965

Phe Ile Ser Phe Tyr Glu Ala Leu Arg Val Asn Ser Ala Val Thr
     1970                  1975                1980

His Leu Arg Gly Phe Leu Leu Leu Phe Ala Thr Val Arg Val Trp
     1985                  1990                1995

Asp Leu Leu Arg His His Ala Gln Leu Gln Val Ile Asn Lys Thr
     2000                  2005                2010

Leu Ser Lys Ala Trp Asp Glu Val Leu Gly Phe Ile Leu Ile Ile
     2015                  2020                2025

Val Val Leu Leu Ser Ser Tyr Ala Met Thr Phe Asn Leu Leu Phe
     2030                  2035                2040

Gly Trp Ser Ile Ser Asp Tyr Gln Ser Phe Phe Arg Ser Ile Val
     2045                  2050                2055

Thr Val Val Gly Leu Leu Met Gly Thr Ser Lys His Lys Glu Val
     2060                  2065                2070

Ile Ala Leu Tyr Pro Ile Leu Gly Ser Leu Leu Val Leu Ser Ser
     2075                  2080                2085

Ile Ile Leu Met Gly Leu Val Ile Ile Asn Leu Phe Val Ser Ala
     2090                  2095                2100

Ile Leu Ile Ala Phe Gly Lys Glu Arg Lys Ala Cys Glu Lys Glu
     2105                  2110                2115

Ala Thr Leu Thr Asp Met Leu Leu Gln Lys Leu Ser Ser Leu Leu
     2120                  2125                2130

Gly Ile Arg Leu His Gln Asn Pro Ser Glu Glu His Ala Asp Asn
     2135                  2140                2145

Thr Gly Tyr
     2150

<210> SEQ ID NO 3
<211> LENGTH: 5199
<212> TYPE: DNA
<213> ORGANISM: Homo sapiens

<400> SEQUENCE: 3

-continued

```
atgttcttca aaggaggaag ctggctttgg ttatacatca gaacaagtat tattctagga    60
agtgagctaa acagcccagc accacatggg caaaataatt gttaccagct taacagattt   120
caatgcagct ttgaggaagc acagcattac tgtcatgtgc agagaggatt cctagctcat   180
atttggaaca aggaagttca agatctcatc cgggactatc tggaagaagg aaagaagtgg   240
tggattgggc aaaatgtaat gccattgaaa aagcatcaag acaacaaata cccagcagac   300
gttgcagcca acgggccccc aaagcccctc agctgcacct acctgtccag aaacttcatt   360
cggatctcat ccaaagggga caagtgctta ctgaaatact atttcatttg ccagactggt   420
gacttttttgg acggagatgc ccattatgaa agaaatggaa ataattccca tttgtaccag   480
agacacaaga agacaaaaag aggagttgca atagcaagag acaaaatgcc cccaggacct   540
ggtcatcttc aaccacatg tcactatcct cttcctgctc atctttccaa gaccctgtgt    600
catcccatca gccagtttcc ttcagtacta tcaagtatca catcacaggt aacatcagcc   660
gcatctgaac ccagcagcca gcctctccct gtgataacac agctcaccat gcccgtgtct   720
gtcacgcatg ctgggcaatc tctggcagaa acaacttcaa gcccaaagga agaaggtcat   780
ccgaatacct tcacctctta tctacaagtg tcattgcaga aggcatctgg tcaggtcata   840
gatgagatag cagggaactt cagcagagca gttcatggtt tgcaagctct taacaaacta   900
caggaagctt gtgagttcct ccagaaacta acagccttaa ccccaagatt ttctaagcca   960
gctcaggtta atctcatcaa ttcccttatt tacctgagtg aggagttact caggatccca  1020
tttcagaaca caacagtct gggcttcaaa gttcctccaa ctgtctgccc ctttcattcc   1080
ctcaacaatg tcaccaaagc tggagaagga agttggctgg aatccaagcg tcatactgag  1140
ccggtagaag acatcctgga aatgtccttg gtggagtttg gaatatcgg ggaagcattt   1200
ctagagcaga accagtctcc cgagtcttca gtgactttga cctctgccaa tgctactctg  1260
ctgctgagca gacaaaacat atcaacttta ccgctgagct cttacactct gggtcaccca  1320
gcccctgtga ggctaggctt tccgtcggct ttagctttga aggagctctt gaataaacat  1380
ccaggagtta atgtccaaat aacaggacta gctttcaatc ccttcaagga tttggacaac  1440
agaaacattg ttggaagcat tggaagtgtg ttactaagcg ctaatcgtaa attgctccaa  1500
gtccatgatt taatggagga cattgagatc atgctctgga gaaatgttag cttggaaacc  1560
catcccacca gcctcaacat gagcacacat cagcttacaa tcacagtgaa cgtcacttcc  1620
ttggagaaat ccttgatagt gagcatagat cctgacagtc ccctttttaat gacactctac  1680
ctggggttcc agtatcagcc taactgcact cacttccacc tgaacatcac ccttccaaag  1740
gataaggtgt ggcaaaaaga tgaggagtac acgtgggtgc tgaatccaga gcatctgcag  1800
cacgggattg gcacctacta tataacagct gtgctgagtg agaggcagga gggtgctcag  1860
cagacaccca gcttggtctc ggtcatcacc gccgtcactc agtgttacta ctgggagatc  1920
cacaaccaga catggagcag cgccggatgc caagttgggc cacagagcac aattctgagg  1980
acacagtgtc tctgtaacca cctgaccttc tttgccagcg acttctttgt cgtgcccagg  2040
accgtgaatg ttgaagacac gatcaaactg ttccttcgcg tgaccaacaa tcctgttggg  2100
gtgtcactgc tggccagcct tttaggattt tatgtgatca cagttgtgtg ggctcggaaa  2160
aaggatcaag cagatatgca gaaggtgaag gtcactgtcc tggctgataa tgaccccagc  2220
gctcaatttc actaccttat tcaggtctac accggatatc gaagaagcgc tgctacaaca  2280
gctaaggttg tcatcaccct ctatggatca gagggacgga gtgagcccca tcacctctgt  2340
gacccccaga agacagtctt tgaacgaggg ggcctggatg tcttccttct caccacttgg  2400
```

```
acctctctag ggaacctgca cagccttcgg ctctggcatg acaattctgg cgtcagtccc   2460
tcctggtatg tcagccaggt aattgtctgt gacatggcag ttaagaggaa gtggcatttc   2520
ctgtgcaatt gctggctggc tgtggacctc ggagactgtg agcttgaccg ggtcttcatc   2580
ccagtttcaa agagagagct cttttccttt agacatctgt tttcctccat gattgtggaa   2640
aagttcaccc aggattatct gtggctttca attgcaactc ggcatccctg aaccagttt   2700 acaagggtcc aacggctgtc ttgctgcatg acactgctac tctgcaacat ggtcatcaat   2760
gttatgttct ggaagataaa cagcaccact gccaagagag atgagcaaat gcgtccattt   2820
gctgtggcct ggtctgaact gctggtcagc atccatactg ctgtcatcct cttcccaatc   2880
aatcttgtca tagggcggct cttcccgttg attgagccac aggagactct gcccctcttt   2940
cctcccatcc aggcctcctg cctctcagat gcttctgttg agcctctctc tgccacaatg   3000
gtagttgagg aattaaagga aactgtgaga ttcctgctca ggagaaatac atacctactc   3060
tccaagtgtg agcagccgcc atggagttct gggacatta ctaagctggt gaaacttta   3120 tccagcctcg tatcatctca cttggagggt caaggctgtc atcagcaggg agagcgccac   3180
tgggcacgtg ttgttcctga aaaccaccat catttctgct gttacctgca tagagttctg   3240
cagaggctga atctcactt aggcacgctg ggtctcaccc agggtcacca gtcctgtgac   3300
ttcctagatg cagccagcca acttcaaaaa ctccaggaac tcttggaaac acatattctt   3360
cccacggagc aagagccatc cagggaagtc accagttttg ccatcctgag ctcagaagaa   3420 ggaaaaagc ccatctcaaa tggcctgtcc aaatggttga cttcagtctg ctggctcctc   3480
ttaggtttca ctagcctggc ttcagccttt tttacagcac tttatagctt ggaattgagc   3540
aaagaccaag ccaccagctg gatgatttca attattttat cagtgcttca gaacatcttc   3600
atcagccagc cagtaaaggt ggtcttcttc acattcttat actcactgat gatgagcagg   3660
atgccacggt taacaaaga gaatgaacaa caaacaaaga ggatcttggc actcttggca   3720
aaatgttctt cgtcagtacc aggttcaaga gataagaaca ccccgtcta tgtagcccca   3780 gctataaata gtccaactaa gcacccagaa agaaccttga aaagaagaa actcttcaag   3840 ctgactggag atattttggt acaaatcctc ttccttaccc tgttgatgac tgcaatctac   3900
tctgcaaaga actccaatag attttaccte caccaagcta tctggaagac attttcgcac   3960
cagttctcgg aaatcaaact tcttcaggat ttctacccct gggccaatca tatccttctt   4020
cctagcctgt atggggatta cagaggtaag aatgcagtcc tggagcccag tcattgcaaa   4080
tgtggggtac aattaattttt ccaaataccc cgtaccaaga cctatgagaa agtggacgaa   4140
ggtcagctgg cgttttgtga taacggccat acctgtgggc gtcccaagag cctattccct   4200
ggacttcatc taaggaggtt cagttacatc tgttcaccca ggcccatggt gctgattccc   4260
actgatgagc ttcacgaaag gctgacaagc aagaatgaga atggattcag ttacatcatg   4320
agaggtgctt tcttcaccctc tttgagactg gaaagcttca cttcccttca gatgtcaaag   4380
aagggctgtg tctggtctat catctcacaa gtcatctatt atctactggt ctgttactat   4440
gccttcatac agggttgtca gctgaaacag cagaagtgga ggttcttcac tgggaaaaga   4500
aacattctgg acacaagtat aatcctcatt agcttcatcc tcctggggct tgacatgaag   4560
agtatttctc tacataagaa aaacatggca cgataccgcg atgaccagga cagattcatc   4620
agcttctatg aggcagtaaa agtgaactct gctgcgactc accttgtggg cttcccggtt   4680
ctcctggcaa ctgttcagtt atggaacctg ctgcgtcata gccccaggct gcgggtcatc   4740
agcaggacac tgagccgagc ctgggacgag gtggtgggct ttctgctgat catcctaatc   4800
```

-continued

```
ctgctgacag gctatgccat tgcctttaac ctgctgtttg gatgcagcat ctctgactac      4860
cggacatttt tcagctcagc agtgactgtt gttggtctcc tgatgggaat ttctcaccaa      4920
gaggaggttt tcgctttaga cccagtcctg gcacctttc tgatcctcac cagtgtcatc       4980
ttgatggtac ttgtggtaat taatcttttc gtttcggcca ttctcatggc ctttggaaaa      5040
gaaagaaagt cgcttaagaa agaagctgca ctaatagata cactgctaca gaagctctca      5100
aatttgttag gaatcagttg gccccaaaaa acctcatctg agcaagcagc cacgacagca      5160
gtgggcagtg acactgaagt tttagatgaa ctaccttaa                             5199
```

<210> SEQ ID NO 4
<211> LENGTH: 1732
<212> TYPE: PRT
<213> ORGANISM: Homo sapiens

<400> SEQUENCE: 4

```
Met Phe Phe Lys Gly Gly Ser Trp Leu Trp Leu Tyr Ile Arg Thr Ser
1               5                   10                  15

Ile Ile Leu Gly Ser Glu Leu Asn Ser Pro Ala Pro His Gly Gln Asn
            20                  25                  30

Asn Cys Tyr Gln Leu Asn Arg Phe Gln Cys Ser Phe Glu Glu Ala Gln
        35                  40                  45

His Tyr Cys His Val Gln Arg Gly Phe Leu Ala His Ile Trp Asn Lys
    50                  55                  60

Glu Val Gln Asp Leu Ile Arg Asp Tyr Leu Glu Glu Gly Lys Lys Trp
65                  70                  75                  80

Trp Ile Gly Gln Asn Val Met Pro Leu Lys Lys His Gln Asp Asn Lys
                85                  90                  95

Tyr Pro Ala Asp Val Ala Ala Asn Gly Pro Pro Lys Pro Leu Ser Cys
            100                 105                 110

Thr Tyr Leu Ser Arg Asn Phe Ile Arg Ile Ser Ser Lys Gly Asp Lys
        115                 120                 125

Cys Leu Leu Lys Tyr Tyr Phe Ile Cys Gln Thr Gly Asp Phe Leu Asp
    130                 135                 140

Gly Asp Ala His Tyr Glu Arg Asn Gly Asn Asn Ser His Leu Tyr Gln
145                 150                 155                 160

Arg His Lys Lys Thr Lys Arg Gly Val Ala Ile Ala Arg Asp Lys Met
                165                 170                 175

Pro Pro Gly Pro Gly His Leu Pro Thr Thr Cys His Tyr Pro Leu Pro
            180                 185                 190

Ala His Leu Ser Lys Thr Leu Cys His Pro Ile Ser Gln Phe Pro Ser
        195                 200                 205

Val Leu Ser Ser Ile Thr Ser Gln Val Thr Ser Ala Ala Ser Glu Pro
    210                 215                 220

Ser Ser Gln Pro Leu Pro Val Ile Thr Gln Leu Thr Met Pro Val Ser
225                 230                 235                 240

Val Thr His Ala Gly Gln Ser Leu Ala Glu Thr Thr Ser Ser Pro Lys
                245                 250                 255

Glu Glu Gly His Pro Asn Thr Phe Thr Ser Tyr Leu Gln Val Ser Leu
            260                 265                 270

Gln Lys Ala Ser Gly Gln Val Ile Asp Glu Ile Ala Gly Asn Phe Ser
        275                 280                 285

Arg Ala Val His Gly Leu Gln Ala Leu Asn Lys Leu Gln Glu Ala Cys
    290                 295                 300
```

-continued

```
Glu Phe Leu Gln Lys Leu Thr Ala Leu Thr Pro Arg Phe Ser Lys Pro
305                 310                 315                 320

Ala Gln Val Asn Leu Ile Asn Ser Leu Ile Tyr Leu Ser Glu Glu Leu
            325                 330                 335

Leu Arg Ile Pro Phe Gln Asn Asn Ser Leu Gly Phe Lys Val Pro
                340                 345                 350

Pro Thr Val Cys Pro Phe His Ser Leu Asn Asn Val Thr Lys Ala Gly
            355                 360                 365

Glu Gly Ser Trp Leu Glu Ser Lys Arg His Thr Glu Pro Val Glu Asp
        370                 375                 380

Ile Leu Glu Met Ser Leu Val Glu Phe Gly Asn Ile Gly Glu Ala Phe
385                 390                 395                 400

Leu Glu Gln Asn Gln Ser Pro Glu Ser Ser Val Thr Leu Thr Ser Ala
                405                 410                 415

Asn Ala Thr Leu Leu Leu Ser Arg Gln Asn Ile Ser Thr Leu Pro Leu
            420                 425                 430

Ser Ser Tyr Thr Leu Gly His Pro Ala Pro Val Arg Leu Gly Phe Pro
        435                 440                 445

Ser Ala Leu Ala Leu Lys Glu Leu Leu Asn Lys His Pro Gly Val Asn
450                 455                 460

Val Gln Ile Thr Gly Leu Ala Phe Asn Pro Phe Lys Asp Leu Asp Asn
465                 470                 475                 480

Arg Asn Ile Val Gly Ser Ile Gly Ser Val Leu Leu Ser Ala Asn Arg
                485                 490                 495

Lys Leu Leu Gln Val His Asp Leu Met Glu Asp Ile Glu Ile Met Leu
            500                 505                 510

Trp Arg Asn Val Ser Leu Glu Thr His Pro Thr Ser Leu Asn Met Ser
        515                 520                 525

Thr His Gln Leu Thr Ile Thr Val Asn Val Thr Ser Leu Glu Lys Ser
    530                 535                 540

Leu Ile Val Ser Ile Asp Pro Asp Ser Pro Leu Leu Met Thr Leu Tyr
545                 550                 555                 560

Leu Gly Phe Gln Tyr Gln Pro Asn Cys Thr His Phe His Leu Asn Ile
                565                 570                 575

Thr Leu Pro Lys Asp Lys Val Trp Gln Lys Asp Glu Glu Tyr Thr Trp
            580                 585                 590

Val Leu Asn Pro Glu His Leu Gln His Gly Ile Gly Thr Tyr Tyr Ile
        595                 600                 605

Thr Ala Val Leu Ser Glu Arg Gln Glu Gly Ala Gln Gln Thr Pro Ser
    610                 615                 620

Leu Val Ser Val Ile Thr Ala Val Thr Gln Cys Tyr Tyr Trp Glu Ile
625                 630                 635                 640

His Asn Gln Thr Trp Ser Ser Ala Gly Cys Gln Val Gly Pro Gln Ser
                645                 650                 655

Thr Ile Leu Arg Thr Gln Cys Leu Cys Asn His Leu Thr Phe Phe Ala
            660                 665                 670

Ser Asp Phe Phe Val Val Pro Arg Thr Val Asn Val Glu Asp Thr Ile
        675                 680                 685

Lys Leu Phe Leu Arg Val Thr Asn Asn Pro Val Gly Val Ser Leu Leu
    690                 695                 700

Ala Ser Leu Leu Gly Phe Tyr Val Ile Thr Val Val Trp Ala Arg Lys
705                 710                 715                 720

Lys Asp Gln Ala Asp Met Gln Lys Val Lys Val Thr Val Leu Ala Asp
                725                 730                 735
```

-continued

Asn Asp Pro Ser Ala Gln Phe His Tyr Leu Ile Gln Val Tyr Thr Gly
        740                 745                 750

Tyr Arg Arg Ser Ala Ala Thr Thr Ala Lys Val Val Ile Thr Leu Tyr
        755                 760             765

Gly Ser Glu Gly Arg Ser Glu Pro His His Leu Cys Asp Pro Gln Lys
        770             775                 780

Thr Val Phe Glu Arg Gly Gly Leu Asp Val Phe Leu Leu Thr Thr Trp
785                 790                 795                 800

Thr Ser Leu Gly Asn Leu His Ser Leu Arg Leu Trp His Asp Asn Ser
            805                 810                 815

Gly Val Ser Pro Ser Trp Tyr Val Ser Gln Val Ile Val Cys Asp Met
            820                 825                 830

Ala Val Lys Arg Lys Trp His Phe Leu Cys Asn Cys Trp Leu Ala Val
            835                 840                 845

Asp Leu Gly Asp Cys Glu Leu Asp Arg Val Phe Ile Pro Val Ser Lys
850                 855                 860

Arg Glu Leu Phe Ser Phe Arg His Leu Phe Ser Ser Met Ile Val Glu
865                 870                 875                 880

Lys Phe Thr Gln Asp Tyr Leu Trp Leu Ser Ile Ala Thr Arg His Pro
                885                 890                 895

Trp Asn Gln Phe Thr Arg Val Gln Arg Leu Ser Cys Cys Met Thr Leu
                900                 905                 910

Leu Leu Cys Asn Met Val Ile Asn Val Met Phe Trp Lys Ile Asn Ser
            915                 920                 925

Thr Thr Ala Lys Arg Asp Glu Gln Met Arg Pro Phe Ala Val Ala Trp
            930                 935                 940

Ser Glu Leu Leu Val Ser Ile His Thr Ala Val Ile Leu Phe Pro Ile
945                 950                 955                 960

Asn Leu Val Ile Gly Arg Leu Phe Pro Leu Ile Glu Pro Gln Glu Thr
                965                 970                 975

Leu Pro Leu Phe Pro Pro Ile Gln Ala Ser Cys Leu Ser Asp Ala Ser
            980                 985                 990

Val Glu Pro Leu Ser Ala Thr Met Val Val Glu Glu Leu Lys Glu Thr
                995                 1000                1005

Val Arg Phe Leu Leu Arg Arg Asn Thr Tyr Leu Leu Ser Lys Cys
    1010                1015                1020

Glu Gln Pro Pro Trp Ser Ser Trp Asp Ile Thr Lys Leu Val Lys
    1025                1030                1035

Leu Leu Ser Ser Leu Val Ser Ser His Leu Glu Gly Gln Gly Cys
    1040                1045                1050

His Gln Gln Gly Glu Arg His Trp Ala Arg Val Val Pro Glu Asn
    1055                1060                1065

His His His Phe Cys Cys Tyr Leu His Arg Val Leu Gln Arg Leu
    1070                1075                1080

Lys Ser His Leu Gly Thr Leu Gly Leu Thr Gln Gly His Gln Ser
    1085                1090                1095

Cys Asp Phe Leu Asp Ala Ala Ser Gln Leu Gln Lys Leu Gln Glu
    1100                1105                1110

Leu Leu Glu Thr His Ile Leu Pro Thr Glu Gln Glu Pro Ser Arg
    1115                1120                1125

Glu Val Thr Ser Phe Ala Ile Leu Ser Ser Glu Glu Gly Lys Lys
    1130                1135                1140

Pro Ile Ser Asn Gly Leu Ser Lys Trp Leu Thr Ser Val Cys Trp

```
                    1145                1150               1155

Leu Leu Leu Gly Phe Thr Ser Leu Ala Ser Ala Phe Phe Thr Ala
    1160                1165               1170

Leu Tyr Ser Leu Glu Leu Ser Lys Asp Gln Ala Thr Ser Trp Met
    1175                1180               1185

Ile Ser Ile Ile Leu Ser Val Leu Gln Asn Ile Phe Ile Ser Gln
    1190                1195               1200

Pro Val Lys Val Val Phe Phe Thr Phe Leu Tyr Ser Leu Met Met
    1205                1210               1215

Ser Arg Met Pro Arg Leu Asn Lys Glu Asn Glu Gln Gln Thr Lys
    1220                1225               1230

Arg Ile Leu Ala Leu Leu Ala Lys Cys Ser Ser Ser Val Pro Gly
    1235                1240               1245

Ser Arg Asp Lys Asn Asn Pro Val Tyr Val Ala Pro Ala Ile Asn
    1250                1255               1260

Ser Pro Thr Lys His Pro Glu Arg Thr Leu Lys Lys Lys Lys Leu
    1265                1270               1275

Phe Lys Leu Thr Gly Asp Ile Leu Val Gln Ile Leu Phe Leu Thr
    1280                1285               1290

Leu Leu Met Thr Ala Ile Tyr Ser Ala Lys Asn Ser Asn Arg Phe
    1295                1300               1305

Tyr Leu His Gln Ala Ile Trp Lys Thr Phe Ser His Gln Phe Ser
    1310                1315               1320

Glu Ile Lys Leu Leu Gln Asp Phe Tyr Pro Trp Ala Asn His Ile
    1325                1330               1335

Leu Leu Pro Ser Leu Tyr Gly Asp Tyr Arg Gly Lys Asn Ala Val
    1340                1345               1350

Leu Glu Pro Ser His Cys Lys Cys Gly Val Gln Leu Ile Phe Gln
    1355                1360               1365

Ile Pro Arg Thr Lys Thr Tyr Glu Lys Val Asp Glu Gly Gln Leu
    1370                1375               1380

Ala Phe Cys Asp Asn Gly His Thr Cys Gly Arg Pro Lys Ser Leu
    1385                1390               1395

Phe Pro Gly Leu His Leu Arg Arg Phe Ser Tyr Ile Cys Ser Pro
    1400                1405               1410

Arg Pro Met Val Leu Ile Pro Thr Asp Glu Leu His Glu Arg Leu
    1415                1420               1425

Thr Ser Lys Asn Glu Asn Gly Phe Ser Tyr Ile Met Arg Gly Ala
    1430                1435               1440

Phe Phe Thr Ser Leu Arg Leu Glu Ser Phe Thr Ser Leu Gln Met
    1445                1450               1455

Ser Lys Lys Gly Cys Val Trp Ser Ile Ile Ser Gln Val Ile Tyr
    1460                1465               1470

Tyr Leu Leu Val Cys Tyr Tyr Ala Phe Ile Gln Gly Cys Gln Leu
    1475                1480               1485

Lys Gln Gln Lys Trp Arg Phe Thr Gly Lys Arg Asn Ile Leu
    1490                1495               1500

Asp Thr Ser Ile Ile Leu Ile Ser Phe Ile Leu Leu Gly Leu Asp
    1505                1510               1515

Met Lys Ser Ile Ser Leu His Lys Lys Asn Met Ala Arg Tyr Arg
    1520                1525               1530

Asp Asp Gln Asp Arg Phe Ile Ser Phe Tyr Glu Ala Val Lys Val
    1535                1540               1545
```

-continued

| | | | | | | | | | | |
|---|---|---|---|---|---|---|---|---|---|---|
|Asn|Ser|Ala|Ala|Thr|His|Leu|Val|Gly|Phe|Pro|Val|Leu|Leu|Ala|
| |1550| | | |1555| | | |1560| |

Thr Val Gln Leu Trp Asn Leu Leu Arg His Ser Pro Arg Leu Arg
    1565            1570            1575

Val Ile Ser Arg Thr Leu Ser Arg Ala Trp Asp Glu Val Val Gly
    1580            1585            1590

Phe Leu Leu Ile Ile Leu Ile Leu Leu Thr Gly Tyr Ala Ile Ala
    1595            1600            1605

Phe Asn Leu Leu Phe Gly Cys Ser Ile Ser Asp Tyr Arg Thr Phe
    1610            1615            1620

Phe Ser Ser Ala Val Thr Val Val Gly Leu Leu Met Gly Ile Ser
    1625            1630            1635

His Gln Glu Glu Val Phe Ala Leu Asp Pro Val Leu Gly Thr Phe
    1640            1645            1650

Leu Ile Leu Thr Ser Val Ile Leu Met Val Leu Val Val Ile Asn
    1655            1660            1665

Leu Phe Val Ser Ala Ile Leu Met Ala Phe Gly Lys Glu Arg Lys
    1670            1675            1680

Ser Leu Lys Lys Glu Ala Ala Leu Ile Asp Thr Leu Leu Gln Lys
    1685            1690            1695

Leu Ser Asn Leu Leu Gly Ile Ser Trp Pro Gln Lys Thr Ser Ser
    1700            1705            1710

Glu Gln Ala Ala Thr Thr Ala Val Gly Ser Asp Thr Glu Val Leu
    1715            1720            1725

Asp Glu Leu Pro
    1730

<210> SEQ ID NO 5
<211> LENGTH: 3297
<212> TYPE: DNA
<213> ORGANISM: Mus musculus

<400> SEQUENCE: 5

```
cgaggttgaa aggatcagct gctcttagac aatactgcct gggctctctg ctaccagtgt    60
cagtctgggt cttttgtccct gtgtctcctg tgagagtggg cacctgtggt ggcaggtttc   120
tacctcctgt ccccatgaat agtatggaaa gccccaagaa tcaggagcta caaaccctgg   180
ggaacagagc ctgggacaat cctgcctaca gcgaccctcc ttccccgaac aggacgctga   240
ggatctgcac tgtctccagt gtggctctcc ctgagactca acccaaaaag ccagaagtca   300
gatgccagga gaagacacag agaaccctgg tgtccagctg ctgtctccat atctgtcgga   360
gcatcagagg actgtggggg acaacgctga ctgagaacac agccgagaac agggagcttt   420
atgtcaagac caccctaagg gagcttgtgg tatacatagt gttcctcgtg gacgtctgtc   480
tgttgaccta cggaatgaca agttctagtg cctattacta caccaaagtg atgtctgaat   540
tgtttctaca caccccatcc gactctggag tctccttcca aaccatcagc agcatgtcag   600
acttctggga ttttgctcag ggcccactcc tggacagttt gtactggaca aagtggtaca   660
acaaccagag cctggggcgt ggctcccact ccttcatcta tatgagaaac ctgctcctgg   720
gagccccaag gttgcggcac gtgcgcgtgc gcaatgactc ctgtgtggtt catgaagact   780
tccggggagga catttttgaac tgttatgatg tgtactcgcc ggacaaagaa gatcagctcc   840
cctttggacc tcagaacggc acagcgtgga cataccattc ccagaatgag ctgggtggct   900
cctcccactg gggcaggctc acaagctaca gcgggggtgg ctactacttg gatcttccag   960
gatcccgaca agccagtgca gaggccctcc aaggactcca ggagggactg tggctggaca  1020
```

```
ggggcactcg ggtggtcttt atcgacttct ccgtctacaa tgccaacatc aatcttttct      1080
gtattctgag actggtggta gagtttccag ccacaggagg gaccatccca tcctggcaga      1140
tccgcacagt taagctgatc cgctatgtga ataactggga cttcttcatt gtgggctgtg      1200
aagttgtctt ctgtgtcttc atcttctatt atgtggtgga ggaaatcctg gaaatccacc      1260
tgcatcggct tcgctacctc agcagcgtct ggaacattct ggacctggtg gtcatccttgc     1320 tctccatcgt ggctgtgggt ttccacatat tccgaaccct ggaagtgaac cgactgatgg      1380
gaaagcttct gcaacagcca gacacgtatg cagactttga gttcctggcc ttctggcaga      1440
ctcaggacaa taacatgaac gcggtcaacc ttttctttgc ttggatcaag atattcaagt      1500
atatcagctt caacaagacc atgacacagc tctcctccac cctggctcga tgtgccaagg      1560
acatcctggg cttcgcagtc atgttcttca ttgtcttctt cgcttacgcc cagcttggtt      1620
acctgctttt tgggacccaa gtggaaaact ttagcacttt cgtcaagtgc attttcactc      1680
agttccggat aatccttggg gattttgact acaatgccat cgacaatgcc aacagaatcc      1740
tgggccctgt gtactttgtc acctatgtct tcttcgtctt cttcgtgctc ctgaacatgt      1800
tcctggccat catcaacgac acatactccg aggtcaagga ggagctggct ggccagaagg      1860
atcagttgca gctttctgac ttcctgaaac agagctacaa caagaccta ctaaggctgc       1920 gcctgaggaa agagcgggtt tctgatgtgc agaaggtcct gaagggtggg gaaccagaga      1980
tccagtttga agatttcacc agcaccttga gggaactggg gcacgaggag cacgagatca      2040
ccgctgcctt caccaggttt gatcaggatg ggaccacat actggatgag gaggagcagg       2100
aacagatgcg gcagggactg gaagaggaga gggtgaccct caatgctgag attgagaacc      2160
taggccggtc tgttggacac agcccccag gcgaattggg cgcggaggct gccagaggac       2220
aaagctgggt ttctggagaa gaattcgaca tgctcacaag gagagttctg cagctgcagt      2280
gtgttctgga aggagttgtg tcccagattg atgctgtagg ctcaaagctg aagatgctgg      2340
agaggaaagg ggagctggct ccctccccag gaatggggga accagctgtt tgggagaacc      2400
tgtataatcc gtcctaggtg tcactccagc tccctgggag ttcagggtgg acaggaggat      2460
ggaaaagggg tcctaaagca acagacagca aattcttctc tctatgcctc ccccacaagc      2520
ctcatctcca tctccatcct catcctttct agggcagcat gtttcatgat ggctgctatg      2580
aagttccccc tgtatctggc cttttcagcc gatgttttg tgtgtagctg ggcagcatgc       2640
ttagacttgt cccttggtgt ttctttatgg agttgcacag ctctgtgaag tagcatttcc      2700
taccaggccc ctctcttcct gggcacttac ttctgccaga gttgattgac atcaacaaca      2760
aacaagaaaa aggagcagat gggaatgact ctccggaaga cctcagacaa ccacgattag      2820
ttaacaggta gaagtccaaa gagtgggcga tggatgtctt cctacgttcc agtaactctt      2880
accctttgtg tgcatcacga tatctgccac tggcaggcat ggttgtgtgt aggaggcctt      2940
ccctttcttt cctcatgggg tttccctgta aaagagaaaa ggaagctgta gggaagaag       3000 attttttgtgt ggtgagattc aacagagga gttaagagtg accccctcca aaggtgaagt     3060
cagtgaattc tggaggagcc tgccttctgg ttcttatgtt ccagcgacca gctgaactg       3120 agggacttc aaacctggaa tcaaacaaaa cctgaaggaa tcaagccaga aaggctatca       3180
ggattcattg atcttttgga ctaatatgtg gtggtctctg gctctcttcg tcataggaca      3240
atgtgaggtt ccaaggtgat tagcaataaa attctttaga aaatcaaaaa aaaaaa         3297
```

<210> SEQ ID NO 6
<211> LENGTH: 760

```
<212> TYPE: PRT
<213> ORGANISM: Mus musculus

<400> SEQUENCE: 6

Met Asn Ser Met Glu Ser Pro Lys Asn Gln Glu Leu Gln Thr Leu Gly
1               5                   10                  15

Asn Arg Ala Trp Asp Asn Pro Ala Tyr Ser Asp Pro Ser Pro Asn
            20                  25                  30

Arg Thr Leu Arg Ile Cys Thr Val Ser Val Ala Leu Pro Glu Thr
        35                  40                  45

Gln Pro Lys Lys Pro Glu Val Arg Cys Gln Glu Lys Thr Gln Arg Thr
    50                  55                  60

Leu Val Ser Ser Cys Cys Leu His Ile Cys Arg Ser Ile Arg Gly Leu
65                  70                  75                  80

Trp Gly Thr Thr Leu Thr Glu Asn Thr Ala Glu Asn Arg Glu Leu Tyr
                85                  90                  95

Val Lys Thr Thr Leu Arg Glu Leu Val Val Tyr Ile Val Phe Leu Val
            100                 105                 110

Asp Val Cys Leu Leu Thr Tyr Gly Met Thr Ser Ser Ala Tyr Tyr
            115                 120                 125

Tyr Thr Lys Val Met Ser Glu Leu Phe Leu His Thr Pro Ser Asp Ser
    130                 135                 140

Gly Val Ser Phe Gln Thr Ile Ser Ser Met Ser Asp Phe Trp Asp Phe
145                 150                 155                 160

Ala Gln Gly Pro Leu Leu Asp Ser Leu Tyr Trp Thr Lys Trp Tyr Asn
                165                 170                 175

Asn Gln Ser Leu Gly Arg Gly Ser His Ser Phe Ile Tyr Tyr Glu Asn
            180                 185                 190

Leu Leu Leu Gly Ala Pro Arg Leu Arg His Val Arg Val Arg Asn Asp
        195                 200                 205

Ser Cys Val Val His Glu Asp Phe Arg Glu Asp Ile Leu Asn Cys Tyr
210                 215                 220

Asp Val Tyr Ser Pro Asp Lys Glu Asp Gln Leu Pro Phe Gly Pro Gln
225                 230                 235                 240

Asn Gly Thr Ala Trp Thr Tyr His Ser Gln Asn Glu Leu Gly Gly Ser
                245                 250                 255

Ser His Trp Gly Arg Leu Thr Ser Tyr Ser Gly Gly Tyr Tyr Leu
            260                 265                 270

Asp Leu Pro Gly Ser Arg Gln Ala Ser Ala Glu Ala Leu Gln Gly Leu
        275                 280                 285

Gln Glu Gly Leu Trp Leu Asp Arg Gly Thr Arg Val Val Phe Ile Asp
    290                 295                 300

Phe Ser Val Tyr Asn Ala Asn Ile Asn Leu Phe Cys Ile Leu Arg Leu
305                 310                 315                 320

Val Val Glu Phe Pro Ala Thr Gly Gly Thr Ile Pro Ser Trp Gln Ile
                325                 330                 335

Arg Thr Val Lys Leu Ile Arg Tyr Val Asn Asn Trp Asp Phe Phe Ile
            340                 345                 350

Val Gly Cys Glu Val Val Phe Cys Val Phe Ile Phe Tyr Tyr Val Val
        355                 360                 365

Glu Glu Ile Leu Glu Ile His Leu His Arg Leu Arg Tyr Leu Ser Ser
    370                 375                 380

Val Trp Asn Ile Leu Asp Leu Val Val Ile Leu Leu Ser Ile Val Ala
385                 390                 395                 400
```

Val Gly Phe His Ile Phe Arg Thr Leu Glu Val Asn Arg Leu Met Gly
                405                 410                 415

Lys Leu Leu Gln Gln Pro Asp Thr Tyr Ala Asp Phe Glu Phe Leu Ala
            420                 425                 430

Phe Trp Gln Thr Gln Asp Asn Asn Met Asn Ala Val Asn Leu Phe Phe
        435                 440                 445

Ala Trp Ile Lys Ile Phe Lys Tyr Ile Ser Phe Asn Lys Thr Met Thr
450                 455                 460

Gln Leu Ser Ser Thr Leu Ala Arg Cys Ala Lys Asp Ile Leu Gly Phe
465                 470                 475                 480

Ala Val Met Phe Phe Ile Val Phe Phe Ala Tyr Ala Gln Leu Gly Tyr
                485                 490                 495

Leu Leu Phe Gly Thr Gln Val Glu Asn Phe Ser Thr Phe Val Lys Cys
            500                 505                 510

Ile Phe Thr Gln Phe Arg Ile Ile Leu Gly Asp Phe Asp Tyr Asn Ala
        515                 520                 525

Ile Asp Asn Ala Asn Arg Ile Leu Gly Pro Val Tyr Phe Val Thr Tyr
530                 535                 540

Val Phe Phe Val Phe Val Leu Leu Asn Met Phe Leu Ala Ile Ile
545                 550                 555                 560

Asn Asp Thr Tyr Ser Glu Val Lys Glu Leu Ala Gly Gln Lys Asp
                565                 570                 575

Gln Leu Gln Leu Ser Asp Phe Leu Lys Gln Ser Tyr Asn Lys Thr Leu
            580                 585                 590

Leu Arg Leu Arg Leu Arg Lys Glu Arg Val Ser Asp Val Gln Lys Val
595                 600                 605

Leu Lys Gly Gly Glu Pro Glu Ile Gln Phe Glu Asp Phe Thr Ser Thr
            610                 615                 620

Leu Arg Glu Leu Gly His Glu His Glu Ile Thr Ala Ala Phe Thr
625                 630                 635                 640

Arg Phe Asp Gln Asp Gly Asp His Ile Leu Asp Glu Glu Glu Gln Glu
                645                 650                 655

Gln Met Arg Gln Gly Leu Glu Glu Glu Arg Val Thr Leu Asn Ala Glu
            660                 665                 670

Ile Glu Asn Leu Gly Arg Ser Val Gly His Ser Pro Pro Gly Glu Leu
        675                 680                 685

Gly Ala Glu Ala Ala Arg Gly Gln Ser Trp Val Ser Gly Glu Glu Phe
690                 695                 700

Asp Met Leu Thr Arg Arg Val Leu Gln Leu Gln Cys Val Leu Glu Gly
705                 710                 715                 720

Val Val Ser Gln Ile Asp Ala Val Gly Ser Lys Leu Lys Met Leu Glu
                725                 730                 735

Arg Lys Gly Glu Leu Ala Pro Ser Pro Gly Met Gly Glu Pro Ala Val
            740                 745                 750

Trp Glu Asn Leu Tyr Asn Pro Ser
        755                 760

<210> SEQ ID NO 7
<211> LENGTH: 3060
<212> TYPE: DNA
<213> ORGANISM: Homo sapiens

<400> SEQUENCE: 7
cagcatcgcc ttttcctccc gtttctcctt ccactcccag ctccacatcc tcctcctatt      60
ctcccctctc ccctcttcaa accccccacct tccagttccc tcacctcccc tttcggctgg    120

```
tccccctgggg cttgcagcaa gagggagaga gagctcctga caggattgat ggtccttccc      180
caccctgtcc tctcatccgc tccctcccca gcaggcacag acatcccct acaaaaggca       240 ggagcccagg ctgtgtggaa acagctgctc tcagacgcct ttccatttgc tctctgctgg      300
ctaggctggg ctgtgcctct gctccctctt cctctagctg agagtgggca cctggggtac      360
cgggcccccc cacctcattc cccatgaatg ctgtgggaag tcctgagggg caggagctgc      420
aaaagctggg gagtggagcc tgggacaacc ccgcctacag tggtccccct tccccacacg      480
ggacgctgag agtctgcacc atctccagca cggggcctct ccagcccaa cccaagaagc       540 ctgaagatga accccaggag acggcataca ggacccaggt gtccagctgc tgcctccata      600
tctgtcaagg catcagagga ctttggggaa caaccctgac tgagaacaca gctgagaacc      660 gggaaccttta tatcaagacc accctgaggg agctgttggt atatattgtg ttcctggtgg     720
acatctgtct actgacctat ggaatgacaa gctccagtgc ttattactac accaaagtga     780
tgtctgagct cttcttacat actccatcag acactggagt ctccttttcag gccatcagca    840 gcatggcgga cttctgggat tttgcccagg gcccactact ggacagtttg tattggacca     900
aatggtacaa caaccagagc ctgggccatg gctcccactc cttcatctac tatgagaaca     960
tgctgctggg ggttccgagg ctgcggcagc taaaggtccg caatgactcc tgtgtggtgc    1020
atgaagactt ccgggaggac attctgagct gctatgatgt ctactctcca gacaaagaag    1080
aacaactccc cttttgggccc ttcaatggca gcgtggac ataccactcg caggatgagt     1140 tgggggggctt ctcccactgg ggcaggctca caagctacag cggaggtggc tactacctgg   1200
accttccagg atcccgacag ggtagtgcag aggctctccg ggcccttcag gaggggctgt    1260
ggctggacag gggcactcga gtggtgttca tcgacttctc agtctacaat gccaatatca    1320 atctttttctg tgtcctgagg ctggtggtgg agtttccagc tacaggaggt gccatcccat   1380
cctggcaaat ccgcacagtc aagctgatcc gctatgtcag caactgggac ttctttatcg    1440
ttggctgtga ggtcatcttc tgcgtcttca tcttctacta tgtggtggaa agatcctgg    1500 agctccacat tcaccggctt cgctacctca gcagcatctg gaacatactg gacctggtgg   1560
tcatcttgct ctccattgtg gctgtgggct tccacatatt ccgaaccctc gaggtgaatc    1620
ggctcatggg gaagctcctg cagcagccaa acacgtatgc agactttgag ttcctcgcct   1680
tctggcagac acagtacaac aacatgaatg ctgtcaacct cttcttcgcc tggatcaaga    1740
tattcaagta catcagcttc aacaaaacca tgacccagct ctcctccacg ctggcccgct    1800
gtgccaagga catcctgggc ttcgccgtca tgttcttcat tgttttcttc gcctatgccc    1860
aactcggcta cctgctttc gggacccaag tggaaaactt tagcactttc atcaagtgca    1920
ttttcactca gttccggata atcctcgggg actttgacta caatgctatc gacaatgcca   1980
accgcatcct gggccctgcc tactttgtca cctatgtctt cttcgtcttc ttcgtgctcc    2040
tgaacatgtt cctggccatc atcaatgaca catattcaga ggtcaaggag gagctggctg   2100
gacagaagga tgagctgcaa ctttctgacc tcctgaaaca gggctacaac aagaccctac    2160
taagactgcg tctgaggaag gagagggttt cggatgtgca gaaggtcctg cagggtgggg   2220
agcaggagat ccagtttgag gatttcacca cacccttaag ggaactggga cacgcagagc    2280
atgaaatcac tgagctcacg gccaccttca ccaagttttga cagagatggg aatcgtattc   2340
tggatgagaa ggaacaggaa aaaatgcgac aggacctgga ggaagagagg gtggccctca    2400
acactgagat tgagaaacta ggccgatcta ttgtgagcag cccacaaggc aaatcgggtc   2460
cagaggctgc cagagcagga ggctgggttt caggagaaga attctacatg ctcacaagga    2520
```

```
gagttctgca gctggagact gtcctggaag gagtagtgtc ccagattgat gctgtaggct    2580
caaagctgaa aatgctggag aggaaggggt ggctggctcc ctccccaggc gtgaaggaac    2640
aagctatttg gaagcacccg cagccagccc cagctgtgac cccagacccc tggggagtcc    2700
agggtgggca ggagagtgag gttccctata aagagaaga ggaagcctta gaggagagga    2760
gactctcccg tggtgagatt ccaacgttgc agaggagtta agtgtgaggc actcccggag    2820
caaagtctat gaaggatctt ctgcaagagg ctgcctcctg gtccactgaa cctggaaact    2880
gagtgggctt taaccaggag ataaaaatgg agcctgaagg gaatcaggca aggaaatgaa    2940
ctcaggattc agagatcttt gaattaatat gtggtgggtt ctgacattat tcttccataa    3000
gaccatgtgg gtttccatgg tggctatcaa taaaactcct taggaaaact taaaaaaaaa    3060
```

<210> SEQ ID NO 8
<211> LENGTH: 805
<212> TYPE: PRT
<213> ORGANISM: Homo sapiens

<400> SEQUENCE: 8

```
Met Asn Ala Val Gly Ser Pro Glu Gly Gln Glu Leu Gln Lys Leu Gly
1               5                   10                  15

Ser Gly Ala Trp Asp Asn Pro Ala Tyr Ser Gly Pro Ser Pro His
            20                  25                  30

Gly Thr Leu Arg Val Cys Thr Ile Ser Ser Thr Gly Pro Leu Gln Pro
        35                  40                  45

Gln Pro Lys Lys Pro Glu Asp Glu Pro Gln Glu Thr Ala Tyr Arg Thr
    50                  55                  60

Gln Val Ser Ser Cys Cys Leu His Ile Cys Gln Gly Ile Arg Gly Leu
65                  70                  75                  80

Trp Gly Thr Thr Leu Thr Glu Asn Thr Ala Glu Asn Arg Glu Leu Tyr
                85                  90                  95

Ile Lys Thr Thr Leu Arg Glu Leu Leu Val Tyr Ile Val Phe Leu Val
            100                 105                 110

Asp Ile Cys Leu Leu Thr Tyr Gly Met Thr Ser Ser Ser Ala Tyr Tyr
        115                 120                 125

Tyr Thr Lys Val Met Ser Glu Leu Phe Leu His Thr Pro Ser Asp Thr
    130                 135                 140

Gly Val Ser Phe Gln Ala Ile Ser Ser Met Ala Asp Phe Trp Asp Phe
145                 150                 155                 160

Ala Gln Gly Pro Leu Leu Asp Ser Leu Tyr Trp Thr Lys Trp Tyr Asn
                165                 170                 175

Asn Gln Ser Leu Gly His Gly Ser His Ser Phe Ile Tyr Tyr Glu Asn
            180                 185                 190

Met Leu Leu Gly Val Pro Arg Leu Arg Gln Leu Lys Val Arg Asn Asp
        195                 200                 205

Ser Cys Val Val His Glu Asp Phe Arg Glu Asp Ile Leu Ser Cys Tyr
    210                 215                 220

Asp Val Tyr Ser Pro Asp Lys Glu Glu Gln Leu Pro Phe Gly Pro Phe
225                 230                 235                 240

Asn Gly Thr Ala Trp Thr Tyr His Ser Gln Asp Glu Leu Gly Phe
                245                 250                 255

Ser His Trp Gly Arg Leu Thr Ser Tyr Ser Gly Gly Tyr Tyr Leu
            260                 265                 270

Asp Leu Pro Gly Ser Arg Gln Gly Ser Ala Glu Ala Leu Arg Ala Leu
        275                 280                 285
```

```
Gln Glu Gly Leu Trp Leu Asp Arg Gly Thr Arg Val Phe Ile Asp
    290                 295                 300

Phe Ser Val Tyr Asn Ala Asn Ile Asn Leu Phe Cys Val Leu Arg Leu
305                 310                 315                 320

Val Val Glu Phe Pro Ala Thr Gly Gly Ala Ile Pro Ser Trp Gln Ile
                325                 330                 335

Arg Thr Val Lys Leu Ile Arg Tyr Val Ser Asn Trp Asp Phe Phe Ile
                340                 345                 350

Val Gly Cys Glu Val Ile Phe Cys Val Phe Ile Phe Tyr Tyr Val Val
                355                 360                 365

Glu Glu Ile Leu Glu Leu His Ile His Arg Leu Arg Tyr Leu Ser Ser
    370                 375                 380

Ile Trp Asn Ile Leu Asp Leu Val Val Ile Leu Leu Ser Ile Val Ala
385                 390                 395                 400

Val Gly Phe His Ile Phe Arg Thr Leu Glu Val Asn Arg Leu Met Gly
                405                 410                 415

Lys Leu Leu Gln Gln Pro Asn Thr Tyr Ala Asp Phe Glu Phe Leu Ala
                420                 425                 430

Phe Trp Gln Thr Gln Tyr Asn Asn Met Asn Ala Val Asn Leu Phe Phe
                435                 440                 445

Ala Trp Ile Lys Ile Phe Lys Tyr Ile Ser Phe Asn Lys Thr Met Thr
450                 455                 460

Gln Leu Ser Ser Thr Leu Ala Arg Cys Ala Lys Asp Ile Leu Gly Phe
465                 470                 475                 480

Ala Val Met Phe Phe Ile Val Phe Phe Ala Tyr Ala Gln Leu Gly Tyr
                485                 490                 495

Leu Leu Phe Gly Thr Gln Val Glu Asn Phe Ser Thr Phe Ile Lys Cys
                500                 505                 510

Ile Phe Thr Gln Phe Arg Ile Ile Leu Gly Asp Phe Asp Tyr Asn Ala
                515                 520                 525

Ile Asp Asn Ala Asn Arg Ile Leu Gly Pro Ala Tyr Phe Val Thr Tyr
                530                 535                 540

Val Phe Phe Val Phe Phe Val Leu Leu Asn Met Phe Leu Ala Ile Ile
545                 550                 555                 560

Asn Asp Thr Tyr Ser Glu Val Lys Glu Glu Leu Ala Gly Gln Lys Asp
                565                 570                 575

Glu Leu Gln Leu Ser Asp Leu Leu Lys Gln Gly Tyr Asn Lys Thr Leu
                580                 585                 590

Leu Arg Leu Arg Leu Arg Lys Glu Arg Val Ser Asp Val Gln Lys Val
                595                 600                 605

Leu Gln Gly Gly Glu Gln Glu Ile Gln Phe Glu Asp Phe Thr Asn Thr
                610                 615                 620

Leu Arg Glu Leu Gly His Ala Glu His Glu Ile Thr Glu Leu Thr Ala
625                 630                 635                 640

Thr Phe Thr Lys Phe Asp Arg Asp Gly Asn Arg Ile Leu Asp Glu Lys
                645                 650                 655

Glu Gln Glu Lys Met Arg Gln Asp Leu Glu Glu Arg Val Ala Leu
                660                 665                 670

Asn Thr Glu Ile Glu Lys Leu Gly Arg Ser Ile Val Ser Ser Pro Gln
                675                 680                 685

Gly Lys Ser Gly Pro Glu Ala Ala Arg Ala Gly Gly Trp Val Ser Gly
    690                 695                 700

Glu Glu Phe Tyr Met Leu Thr Arg Arg Val Leu Gln Leu Glu Thr Val
```

-continued

```
705                     710                     715                     720
Leu Glu Gly Val Val Ser Gln Ile Asp Ala Val Gly Ser Lys Leu Lys
                725                     730                     735

Met Leu Glu Arg Lys Gly Trp Leu Ala Pro Ser Pro Gly Val Lys Glu
            740                     745                     750

Gln Ala Ile Trp Lys His Pro Gln Pro Ala Pro Ala Val Thr Pro Asp
        755                     760                     765

Pro Trp Gly Val Gln Gly Gly Gln Glu Ser Glu Val Pro Tyr Lys Arg
    770                     775                     780

Glu Glu Glu Ala Leu Glu Glu Arg Arg Leu Ser Arg Gly Glu Ile Pro
785                     790                     795                     800

Thr Leu Gln Arg Ser
                805
```

METHODS OF IDENTIFYING LIGANDS TO SOUR-TASTE RECEPTORS COMPRISING PKD1L3 AND PKDPKD2L1

CROSS-REFERENCE TO RELATED APPLICATIONS

This patent application is a Continuation of pending U.S. patent application Ser. No. 13/214,830, filed Aug. 22, 2011, which is a continuation of U.S. patent application Ser. No. 12/632,299, filed Dec. 7, 2009 which issued on Aug. 23, 2011 as U.S. Pat. No. 8,003,384, which is a Continuation of pending U.S. patent application Ser. No. 11/825,941, filed Jul. 10, 2007, now issued as U.S. Pat. No. 7,629,134, which claims priority to expired U.S. Provisional Patent Application No. 60/819,675 filed Jul. 10, 2006, the contents of which are herein incorporated by reference in their entireties.

STATEMENT REGARDING FEDERALLY SPONSORED RESEARCH OR DEVELOPMENT

This invention was made with government support under Grant No. 5 ROI DC005782 awarded by the National Institutes of Health. The government has certain rights in the invention.

FIELD OF THE INVENTION

The present invention relates to sour taste receptors and compositions and methods thereof. In particular, the present invention provides assays and methods of screening for ligands specific for sour taste receptors. Additionally, the present invention provides methods for screening for accessory proteins and mutations, polymorphisms and other potential sour taste receptor protein mutations that are associated with disease states, and therapeutic agents, ligands, and modulators of such proteins. The present invention also provides compositions and methods for modulating sour taste receptors in vitro and in vivo.

BACKGROUND OF THE INVENTION

Flavor is a complex mixture of sensory input composed of taste (gustation), smell (olfaction) and the tactile sensation of food as it is being munched, a characteristic that food scientists often term "mouthfeel." Although people may use the word "taste" to mean "flavor," in the strict sense it is applicable only to the sensations arising from specialized taste cells in the mouth. Scientists generally describe human taste perception in terms of four qualities: saltiness, sourness, sweetness and bitterness. A fifth taste exists as umami, the sensation elicited by glutamate, one of the 20 amino acids that make up the proteins in meat, fish and legumes. Glutamate also serves as a flavor enhancer in the form of the additive monosodium glutamate (MSG).

Animals use taste systems to evaluate the nutritious value, toxicity, sodium content, and acidity of the food they ingest. In vertebrates, taste reception occurs at the top of the taste cells that form taste buds, and each taste bud has an onion-like shape. There are four major taste areas where taste buds are concentrated; on the tongue at the circumvallate papilla, foliate papilla, and fungiform papilla, and the palate (top of the mouth). Circumvallate papillae, found at the very back of the tongue, contain hundreds to thousands of taste buds. By contrast, foliate papillae, localized to the posterior lateral edge of the tongue, contain dozens to hundreds of taste buds. Further, fungiform papillae, located at the front of the tongue, contain only a single or a few taste buds. Each taste bud, depending on the species, contains 50-150 cells, including precursor cells, support cells, and taste receptor cells (Lindemann et al., 1996, Physiol. Rev. 76:718-66). Receptor cells are innervated at their base by afferent nerve endings that transmit information to the taste centers of the cortex through synapses in the brain stem and thalamus. Elucidating the mechanisms of taste cell signaling and information processing is important to understanding the function, regulation, and perception of the sense of taste.

Much progress has been made in unraveling molecular mechanisms of bitter, sweet and umami taste in recent years (Margolskee, 2002, J. Biol. Chem. 277:1-4; Montmayeur and Matsunami, 2002, Curr. Opin. Neurobiol. 12:366-371; Scott, 2004, Curr. Opin. Neurobiol. 14:423-427). However, the molecular basis of sour taste sensation is the most poorly understood of the five basic modalities.

A whole industry exists around trying to disguise or mask unpleasant tastes. In 1879, Ira Remsen noticed that a derivative of coal tar tasted sweet. H is finding led to the development of saccharin, an artificial sweetener today known as Sweet-n-Low Brand® sweetener. Today, many more artificial sweeteners with varying chemical structures are available including Sunett® (acesulfame potassium), NutraSweet® or Equal®(aspartame), Splenda® (sucralose), and Sugaree® (D-Tagatose). However, some of these artificial sweeteners, such as saccharin and aspartame, have been linked with cancer and other medical problems. Natural plant compounds have also been found to mask unpleasant tastes. Miraculin, a protein found in the pulp of the fruit of the miracle berry, an evergreen shrub native to West Africa, has been described as a "sweet-inducing" protein, and is suggested to bind to sweet taste receptors in the mouth when sour substances are present, the result being a strong sweet taste. Miraculin itself has no distinct taste, but the human tongue when exposed to the protein perceives ordinarily sour foods as sweet. Other plant proteins which are being studied as natural sweeteners include, stevia, curculin, mabinlin, monellin, pentadin, brazzein, and thaumatin (Faus, 2000, Appl. Microbiol. Biotechnol. 53:145-151; Kohmura et al., 2002, Pure Appl. Chem. 74:1235-1242). Contrasted to those individuals who prefer sweet tasting products, there are an equal number who seek out the taste of sour, as evidenced by the myriad of sour candy options available for consumption.

Sweeteners, either artificial or natural, find useful application, for example, as sugar substitutes in the weight loss industry, as sugar alternatives for people suffering from diabetes and other diseases where sugar intake is restricted, as additives to foods and beverages, and in the pharmaceutical industry to make medicaments palatable. Clinically, taste disorders are prevalent in patients undergoing chemotherapy and often have a negative impact on the quality of life and nutrition for those patients. Radiation treatment can also damage taste receptors, giving food a metallic taste. Those patients suffering from taste distortion may avoid foods with high nutritional value, such as fresh fruits and vegetables, thereby further depressing their immune functions. A better understanding of the complex and often multifactorial etiology of taste dysfunction would enable the clinician to institute measures to minimize the impact of these disturbing changes. What is needed is a better understanding of sour taste receptor sensation. What is further needed is a better understanding of sour taste receptor function. Additionally, what is needed are methods and assays to screen for, and to use, ligands that can either inhibit or upregulate sour taste receptor.

SUMMARY OF THE INVENTION

The present invention relates to sour taste receptors and compositions and methods thereof. In particular, the present invention provides assays and methods of screening for ligands specific for sour taste receptors. Additionally, the present invention provides methods for screening for accessory proteins and mutations, polymorphisms and other potential sour taste receptor protein mutations that are associated with disease states, and therapeutic agents, ligands, and modulators of such proteins. The present invention also provides compositions and methods for modulating sour taste receptors in vitro and in vivo.

The transient receptor potential (TRP) ion channel subunit genes were first defined in the *Drosophila* visual system, where TRP deficient flies were blinded by intense light as a result of calcium dependent adaptation disruption (Clapham et al., 2002, IUPHAR Compendium, TRP Channels). Since then, TRP ion channels have been implicated in various sensory systems, including vision, smell, pheromone, hearing, touch, osmolarity, thermosensation, and sweet, bitter and umami taste, in diverse animal species ranging from mammals and fish to fruit flies and nematodes (Clapham, 2003, Nature 426:517-524; Montell, 2005, Sci. STKE 2005:re3). Some TRP channels such as vanilloid receptor, TRPV 1, function as receptors for stimuli (high temperature and capsaicin) by themselves, whereas other TRP channels, such as TRPM5, are downstream effectors of G protein coupled sensory receptors.

Two TRP channel family members, PKD1L3 and PKD2L1, are co-expressed in a subset of taste receptor cells in specific taste areas. Cells expressing these molecules are different from bitter, sweet or umami sensing cells. The PKD2L1 proteins are accumulated at the taste pore region, where taste chemicals are detected. Finally, PKD1L3 and PKD2L1 are activated by sour chemicals when co-expressed in heterologous cells. Therefore, PKD1L3 and PKD2L1 heteromers function as sour taste receptors.

In one embodiment, the present invention relates to a method for identifying a sour taste receptor ligand, comprising providing a sample comprising a sour taste receptor, and a test compound, exposing said test compound to said sample and measuring the activity of said sour taste receptor in said sample in response to said test compound. In some embodiments, said sample is a cell line expressing PKD1L3 and PKD2L1. In some embodiments, said cell line is a 293T cell line. In some embodiments, said cell line is derived from a 293T cell line, such as a Hana3A cell line or a 44 cell line. In some embodiments, said PKD1L3 and PKD2L1 are either human or murine. In some embodiments, said test compound is from a list consisting of a naturally occurring molecule, a synthetically derived molecule, or a recombinantly derived molecule.

In one embodiment, the method for identifying a sour taste receptor ligand further comprising a reporting agent. In some embodiments, the method for identifying a sour taste receptor ligand further comprises the step of detecting the presence or absence of a sour taste receptor ligand based upon said reporting agent activity. In some embodiments, said reporting agent is a fluorophore, and said fluorophore is from a group consisting of fluo-4 and fura-red.

In one embodiment, the present invention is a cell that expresses a heterologous sour taste receptor. In some embodiments, said cell line expresses murine or human PKD1L3 and PKD2L1, or combinations thereof. In some embodiments, said cell is a human embryonic kidney 293T cell line.

In some embodiments, the sour taste receptor is modulated, in vivo or in vitro, by the introduction of a modulator (e.g., ligand, chemical, compound, or agent) to a sample or subject such that the sour taste sensation is inhibited or decreased. In other embodiments, the modulator acts to upregulate or increase sour taste sensation. In some embodiments, the modulator is added or applied to a food product (e.g., vegetable, fruit, meat, candy, oils, etc.). In other embodiments, an inhibitor of the sour taste sensation is added or applied as part of a pharmaceutical medicament (e.g., pillules, powders, elixirs, etc.).

DEFINITIONS

Figure 1:
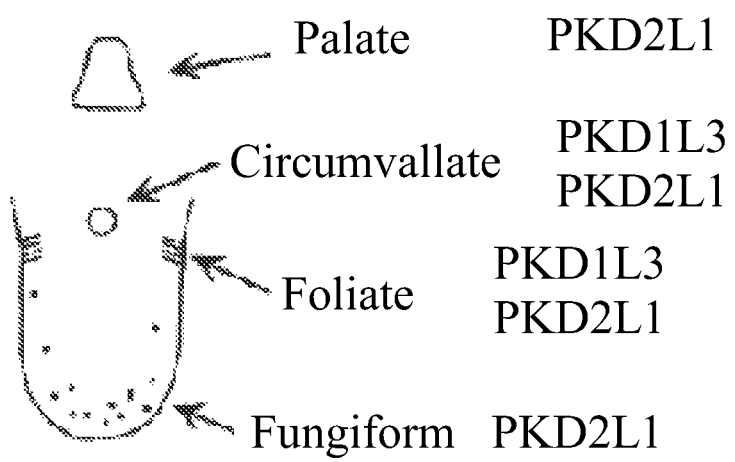
FIG. 1 shows the localization of PKD1L3 and PKD2L1 on the mouse tongue.

The term "test compound" refers to any chemical entity, pharmaceutical, drug, and the like that can be used to treat or prevent a condition, disease, illness, sickness, or disorder of bodily function, or otherwise alter the physiological or cellular status of a sample. Test compounds comprise both known and potential therapeutic compounds. A test compound can be determined to be by screening using the screening methods of the present invention.

The term "sample" as used herein is used in its broadest sense. A sample suspected of containing a protein may comprise a cell, a portion of a tissue, an extract containing one or more proteins and the like.

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284), chloramphenicol acetyltransferase, β-galactosidase, alkaline phosphatase, horse radish peroxidase, and fluorophores such as fluo-4 and fura-red.

The term "siRNAs" refers to short interfering RNAs. Methods for the use of siRNAs are described in U.S. Patent App. No. 20030148519/A1 (herein incorporated by reference in its entirety). In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

As used herein, the term "genetic variation information" or "genetic variant information" refers to the presence or absence of one or more variant nucleic acid sequences (e.g., polymorphism or mutations) in a given allele of a particular gene (e.g., a PKD1L3 or PKD2L1 gene of the present invention).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "recombinant protein" or "recombinant polypeptide" as used herein refers to a protein molecule that is expressed from a recombinant DNA molecule.

The term "native protein" as used herein, is used to indicate a protein that does not contain amino acid residues encoded by vector sequences; that is the native protein contains only those amino acids found in the protein as it occurs in nature. A native protein may be produced by recombinant means or may be isolated from a naturally occurring source.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

DETAILED DESCRIPTION OF THE INVENTION

Bitter, sweet and umami stimuli are detected by G protein coupled receptors. Bitter chemicals are detected by around 30 T2R receptor family members (Adler et al., 2000, Cell 100: 693-702; Chandrashekar et al., 2000, Cell 100:703-711; Matsunami et al., 2000, Nature 404:601-604). Sweet and umami compounds are detected by different combinations of T1R family members. Sugars and sweeteners are detected by T1R2+T1R3 heteromers, whereas umami tasting 1-amino acids are detected by T1R1+T1R3 heteromers (Damak et al., 2003, Science 301:850-853; Kitagawa et al., 2001, Biochem. Biophys. Res. Comm. 283:236-242; Li et al., 2002, Proc. Natl. Acad. Sci. 99:4692-4693; Max et al., 2001, Nat. Genet. 28:58-63; Montmayeur et al., 2001, Nat. Neurosci 4:492-498; Nelson et al., 2002, Nature 416:199-202; Nelson et al., 2001, Cell 106:381-390; Zhao et al., 2003, Cell 115:255-266). Different sets of taste cells express T2R5, T1R2+T1R3, or T1R1+T1R3. Moreover, an animal's preference toward chemicals can be manipulated by misexpressing foreign receptors in different subsets of taste cells. For example, when the artificial RASSL receptor was expressed in T1R2 positive sweet sensing cells, mice were attracted to water containing spiradonine, an agonist for the RASSL receptor, whereas when the same receptor was expressed in T2R expressing bitter sensing cells, the animals avoid spiradoline (Mueller et al., 2005, Nature 434:225-229; Zhao et al., 2003). Thus, taste cells are likely to be "labeled" as bitter, sweet, or umami sensing cells. Nevertheless, both T1R5 and T2R5 express common signal transduction molecules, including PLCb2 and TRPM5, and IP3R-3 (Clapp et al., 2001, Neurosci. 2:6; Miyoshi et al., 2001, Chem. Senses 26:259-265; Perez et al., 2002, Nat. Neurosci. 5:1169-1176; Zhang et al., 2003, Cell 112:293-301).

In contrast to sweet, bitter and umami sensations, molecular mechanisms of sensing sour and salty taste are poorly understood and even confusing, although a number of candidate receptors and transduction mechanisms have been proposed (Miyamoto et al., 2000, Prog. Neurobiol. 62:135-157). For example, acid-sensing ion channel-2 (ASIC2) is proposed to function as a sour receptor in the rat (Ugawa et al, 2003, J. Neurosci. 23:3616-3622; Ugawa et al., 1998, Nature 395:555-556). However, it is not expressed in mouse taste cells and not required for acid sensation (Richter et al., 2004, J. Neurosci. 24:4088-4091). HCN1 and HCN4, members of hyperpolarization-activated cyclic nucleotide gated channels (HCNs) are also candidate sour receptor channels (Stevens et al., 2001, Nature 413:631-635). However, calcium imaging experiments using taste bud slices did not support this possibility, as $Cs^+$, an inhibitor of HCN channels, did not block $Ca^{2+}$ response of taste cells to sour stimuli (Richter et al., 2003, J. Physiol. 547:475-483). Moreover, unlike bitter, sweet and umami taste receptors, S1CS2, HCN1 and JCN4 are all widely expressed in the nervous system (Lingueglia et al., 1997, J. Biol. Chem. 272:29778-29783; Ludwig et al., 1998, Nature 393:587-591; Moosmang et al., 1999, Biol. Chem. 380:975-980).

Among TRP channel families, member of the PKD family (polycystic kidney disease, also called TRPP or polycystins) have unique properties (Delmas et al., 2004, Biochem. Biophys. Res. Commun. 322:1374-1383; Nauli and Zhou, 2004, Bioessays 26:844-856). Their founding members, PKD1 and PKD2, were identified as autosomal dominant polycystic kidney disease genes. PKD1 is a large protein with a long N-terminal extracellular domain followed by 11 transmembrane domains. PKD1 may not form functional ion channels, while PKD2 which has 6 transmembrane domains similar to other TRP members, can function as a non-selective cation channel. Importantly, PKD1 and PKD2 heteromer formation using their intracellular C-terminal regions is required to become a functional receptor/channel (Hanaoka et al., 2000, Nature 408:990-994). The heteromer of PKD1 and PKD2 are thought to sense mechanical flow, osmolarity and unknown extracellular ligand(s). In C. elegans, a PKD1 homolog, Lov-1, and a PKD2 homolog are expressed in male specific sensory neurons, localized at the chemosensory cilia, and are required for male mating behavior thereby suggesting their function as sensory receptors (Barr et al., 2001, Curr. Biol. 11:1341-1346; Barr and Sternberg, 1999, Nature 401:386-389). There are four additional PKD1-like and two additional PKD2-like genes found in the mouse or human genome (Chen et al., 1999, Nature 401:383-386; Guo et al., 2000, Genomics 241-251; Hughes et al., 1999, Hum. Mol. Genet. 8:543-549; Li et al., 2003, Genomics 81:596-608; Nomura et al., 1998, J. Biol. Chem. 273:25967-25973; Yuasa et al., 2002, Genomics 79:376-386), however the biological functions of these PKD related molecules are poorly understood.

Figure 2:
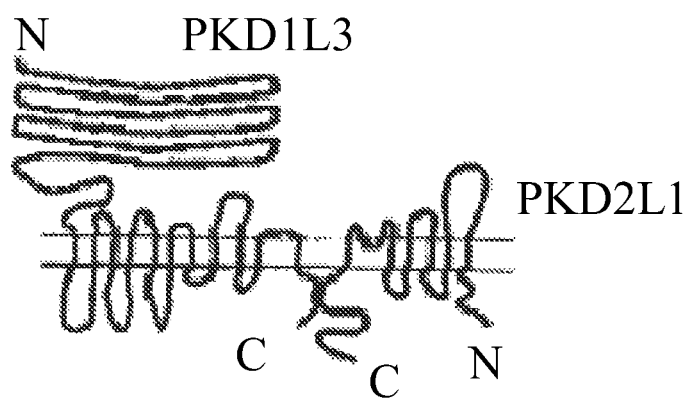
FIG. 2 shows a potential mechanism for cell surface formation of the PKD1L3 and PKD2L1 heteromer.

Characterization of molecular identities that receive taste chemicals is needed to understand the molecular mechanisms underlying taste sensation. Two TRP channel members, PKD1L3 (Genbank Accession Nos. AY164486 (murine, nucleic acid, SEQ ID NO:1), AA032799 (murine, amino acid, SEQ ID NO:2), AY164485 (human, nucleic acid, SEQ ID NO:3) and AA032798 (human, amino acid, SEQ ID NO:4), incorporated herein by reference in their entireties) and PKD2L1 (Genbank Accession Nos. NM_181422 (murine, nucleic acid, SEQ ID NO:5), NP_852087 (murine, amino acid, SEQ ID NO:6), NM_016112 (human, nucleic acid, SEQ ID NO:7) and NP_057196 (human, amino acid, SEQ ID NO:8), incorporated herein by reference in their entireties) are specifically expressed in a subset of taste receptor cells that do not correspond to bitter, sweet or umami sensing cells (FIG. 1). The proteins are localized at the apical tip of taste cells where tastants are detected. PKD1L3 and PKD2L1 heteromer formation (FIG. 2) is required for functional cell surface expression and whenever they are expressed in heterologous cells they are activated by sour solutions. Therefore, PKD1L3 and PKD2L1 function together as sour taste receptors in mammals, although an understanding of the mechanism is not necessary to practice the present invention and the present invention is not limited to any particular mechanism of action.

In one embodiment, the present invention provides methods for detecting ligands, and other modulators, that interact with the sour taste receptor. In some embodiments, the methods are assays that comprise the PKD1L3 and PKD2L1 proteins, or functional fragments or variants thereof. In some embodiments, the assays comprise human PKD1L3 and PKD2L1 proteins, or functional fragments thereof. In some embodiments, these two proteins are co-expressed in tissue culture cells lines, or other cell samples (e.g., gross tissue, tissue explants, primary cells, etc.). In some embodiments, these two proteins are chimeric proteins, whereas one or more of the protein domains is murine in origin while one or more of the protein domains are of human origin. In some embodiments, test compounds suspected, or known to be, ligand to sour taste receptors are applied to the sample and sour taste sensation in the sample is subsequently monitored following application of the test compound. In some embodiments, the monitoring of the sour taste sensation in a sample is performed by monitoring calcium influx via fluorescence, although the present invention is not limited by the manner in which activity or binding is monitored. In some embodiments, the ligand inhibits the sour taste sensation, whereas in other embodiments the ligand enhances the sour taste sensation.

In some embodiments, the PKD1L3 and/or PKD2L1 amino acid sequences are altered or are provided as part of a chimeric peptide sequence, such as with an affinity tag to assist with purification, with a localization tag to assist with intracellular trafficking or localization, and the like). For example, in some embodiments the sequences of the proteins are linked, directly or indirectly, (e.g., via a linker) with an affinity tag (e.g., hemagglutinin A (HA) tag, Rho tag, and the like), for example on the N-terminus of the protein.

In some embodiments, the present invention provides variants or fragments thereof of the wild-type PKD1L3 and/or PKD2L1 gene or gene product sequences. For example, a wild-type gene or gene product has the characteristics of that gene or gene product when isolated from a naturally occurring source. A wild-type gene is that which is most frequently observed in a population and is thus arbitrarily designed the "normal" or "wild-type" form of the gene. In contrast, modified, mutant and variant refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. This is in contrast to synthetic mutants that are changes made in a sequence through human (or machine) intervention.

Variants may be generated by post-translational processing of the protein (e.g., by enzymes present in a producer strain or by means of enzymes or reagents introduced at any stage of a manufacturing process) or by mutation of the structural gene. Mutations may include site deletion, insertion, domain removal and replacement mutations.

Structural and functional equivalents and variants are contemplated with the present invention. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of sensory receptors, such as sour taste receptors PKD1L3 and PKD2L1 disclosed herein that contain conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, $2^{nd}$ ed, WH Freeman and Co., 1981). Whether a change in the amino acid sequence of a peptide results in a functional homolog can be readily determined by assessing the ability of the variant peptide to function in a fashion similar to the reference protein. Peptides having more than one replacement can readily be tested in the same manner.

As well, a variant of the present invention includes "non-conservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

In some embodiments, the methods and compositions of the present invention are combined with compositions and methods of other taste receptors (e.g., sweet, salty, bitter, umami). Examples of taste receptor compositions and methods which can be combined or utilized with the compositions and methods of the present invention include, but are not limited to, those found in the following United States patent and patent applications, all of which are incorporated herein by reference in their entireties; U.S. Pat. Nos. 6,955,887, 6,608,176, 20060019346, 20050287517, 20050084932, 20040248123, 20040348149, 20040229239, 20041219632, 20040209313, 10040209286, 20040191862, 20040175793, 20040175792, 20040171042, 20040132134, 20040132075, 20020164645, 20020151052, 20020037515. These applications also describe screening methods and compound libraries that find use with the present invention.

In one embodiment, the present invention provides methods of identifying modulators of the sour taste receptor. A modulator can be a candidate or test substance that is suspected of modulating (e.g., increasing, decreasing, inhibiting) the activity of the sour taste receptor. As used herein, the terms "candidate substance" and "test substance" are used interchangeably, and each refers to a substance that is suspected to interact with either PKD1L3, PKD2L1 or the heteromer, including any synthetic, recombinant, or natural product or composition. A test substance suspected to interact with either PKD1L3 or PKD2L1 or the heteromer can be evaluated for such an interaction using the methods disclosed herein. In some embodiments, test substances include, but are not limited to peptides, oligomers, nucleic acids (e.g., aptamers), small molecules (e.g., chemical compounds), antibodies or fragments thereof, nucleic acid-protein fusions, any other affinity agent, and combinations thereof. A test substance can additionally comprise a carbohydrate, a vitamin or derivative thereof, a hormone, a neurotransmitter, a virus or receptor binding domain thereof, a pheromone, a toxin, a growth factor, a platelet activation factor, a neuroactive peptide, or a neurohormone.

In some embodiments, a candidate substance elicits no sour taste sensation. In some embodiments, a candidate substance elicits an increased, or enhanced, sour taste sensation. In some embodiments, a candidate substance to be tested can be a purified molecule, a homogenous sample, or a mixture of molecules or compounds. In some embodiments, the test substance is a small molecule. Small molecules may be comprised in compound libraries of diverse or structurally similar compounds (e.g, combinatorial chemistry synthesized libraries). In some embodiments, the test substance will include naturally occurring sour compounds (e.g., derived from plant extracts and the like). Test substances can be obtained or prepared as a library. As used herein, the term "library" means a collection of molecules. A library can contain a few or a large number of different molecules, varying from about ten molecules to several billion molecules or more. A molecule can comprise a naturally occurring molecule, a recombinant molecule, or a synthetic molecule. A plurality of test substances in a library can be assayed simultaneously. Optionally, test substances derived from different libraries can be pooled for simultaneous evaluation. Representative libraries include but are not limited to a peptide library (U.S. Pat. Nos. 6,156,511, 6,107,059, 5,922,545, and 5,223,409), an oligomer library (U.S. Pat. Nos. 5,650,489 and 5,858,670), an aptamer library (U.S. Pat. Nos. 6,180,348 and 5,756,291), a small molecule library (U.S. Pat. Nos. 6,168,912 and 5,738, 996), a library of antibodies or antibody fragments (U.S. Pat. Nos. 6,174,708, 6,057,098, 5,922,254, 5,840,479, 5,780,225, 5,702,892, and 5,667,988), a library of nucleic acid-protein fusions (U.S. Pat. No. 6,214,553), and a library of any other affinity agent that can potentially bind to a T2R76 polypeptide (e.g., U.S. Pat. Nos. 5,948,635, 5,747,334, and 5,498, 538). Additionally, a library can comprise a random collection of molecules. Alternatively, a library can comprise a collection of molecules having a bias for a particular sequence, structure, or conformation (e.g., U.S. Pat. Nos. 5,264,563 and 5,824,483, incorporated herein in their entireties). Methods for preparing libraries containing diverse populations of various types of molecules are known in the art, for example as described in U.S. patents cited herein above. Numerous libraries are also commercially available.

In some embodiments, ligands that inhibit sour taste sensation are used in the pharmaceutical industry to create more palatable medicaments. In some embodiments, ligands that inhibit sour taste sensation are suitable for oral administration and may be presented as adjuvants in capsules, cachets or tablets, wherein the medicament preferably contains a predetermined amount of ligand sufficient to inhibit the sour taste sensation.

In some embodiments, ligands that inhibit sour taste sensation are used with food products and beverages. In some embodiments, ligands that inhibit sour taste sensation are added to, applied to, or applied on, food products that impart a sour taste sensation (e.g., for example, broccoli and green grapes). In some embodiments, ligands that inhibit sour taste sensation are added to beverages (e.g., for example, grapefruit juice, lime juice and lemon juice).

In one embodiment, the present invention relates to compositions and methods relating to RNA inhibition of the sour taste receptor. In some embodiments, the translation of either PKD1L3 or PKD2L1 is inhibited by application of a short interfering siRNA (siRNA). In some embodiments, the siRNA targets the expression of one or both of the murine sour taste receptor proteins. In some embodiments, the siRNA targets the expression of one or both of the human sour taste receptor proteins.

In one embodiment, the present invention relates to compositions and methods for inhibition of the sour taste receptor by using an antibody to either PKD1L3 or PKD2L1, or both, or fragments thereof. In some embodiments, antibodies are administered with pharmaceutical medicaments and treatments. In some embodiments, the antibodies are co-administered with food stuffs (e.g., broccoli, cauliflower, spinach, etc.) that trigger sour taste receptors.

In one embodiment, the present invention relates to compositions and methods for inhibition of the sour taste receptor by using a small molecule to PKD1L3, PKD2L1, or both, or fragments thereof. In some embodiments, the small molecules are administered with pharmaceutical medicaments and treatments. In some embodiments, the small molecules are co-administered with food stuffs (e.g., broccoli, cauliflower, spinach, etc.) that trigger sour taste receptors.

In one embodiment, the methods of the present invention are used to define ligands that enhance sour taste sensation. In some embodiments, ligands that enhance sour taste sensation are added to human consumable products, such as candy, gummy worms, powdered candy, chewing gum, libations and elixirs.

In one embodiment, PKD1L3 and PKD2L1 can be used to created transgenic animals (e.g., mice, rats, hamsters, guinea pigs, ungulates, zebrafish, pigs, birds, etc.). In some embodiments, the transgenic animals are created such that the sour taste receptor is overexpressed. In some embodiments, the transgenic animals are created such that sour taste receptor expression is knocked out (e.g., does not express the receptor). In some embodiments, the transgenic animal has one of PKD1L3 or PKD2L1 genes knocked out. In other embodiments, the transgenic animal has both PKD1L3 and PKD2L1 genes knocked out. In some embodiments, the transgenic animal expresses one or both of human PKD1L3 and PKD2L1. In some embodiments, the transgenic animals express a chimeric protein for PKD1L3, PKD2L1 or both. Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), all patents being incorporated herein by reference in their entireties.

In one embodiment, computer modeling and searching technologies are used to identify compounds, or improvements of already identified compounds, that can modulate the sour taste receptor expression or activity. Having identified such a compound or composition, the active sites or regions are identified. Such active sites might typically be ligand binding sites, such as the interaction domains of a portion of a ligand with the sour taste receptor itself (e.g., either PKD1L3 or PKD2L1 alone, or the heteromer), or the interaction domains of a ligand with the wild-type sour taste receptor in comparison to the interaction domains of ligand with a mutant (e.g., change in the nucleic acid or amino acid sequence, or deletions, insertions, truncations of a gene or protein) sour taste receptor. In some embodiments, the active site can be identified using methods known in the art including, for example, from the amino acid sequences of peptides, from the nucleotide sequences of nucleic acids, or from study of complexes of the relevant compound or composition with its natural ligand. In some embodiments, chemical or X-ray crystallographic methods can be used to find the active site by finding where on the heteromer the complexed ligand is found. In some embodiments, the three dimensional geometric structure of the active site is determined (e.g., by known methods including X-ray crystallography). In further embodiments, solid or liquid phase nuclear magnetic resonance can be used to determine certain intra-molecular distances. In some embodiments, partial or complete geometric structures of the heteromer alone, or with ligand interaction, is accomplished by high resolution electron microscopy. For example, the geometric structures can be measured with a complexed ligand, natural or artificial, thereby increasing the accuracy of the active site structure. In another embodiment, the structure of the wild-type sour taste receptor is compared to that of a mutant sour taste receptor. In some embodiments, rather than solve the entire structure, the structure is solved for the protein domains that are changed between the wild type and mutant sour taste receptor.

In one embodiment, the present invention provides cells expressing wild type or chimeric PKD1L3 and/or PKD2L1 proteins. In some embodiments, the cells are human cells. In some embodiments, the human cells are human embryonic kidney 293T cells. In some embodiments, the cells are murine in origin. In some embodiments, the wild type proteins are murine in origin, whereas in other embodiments the wild type proteins are human in origin. In some embodiments, the chimeric protein contains domains, regions, or fragments of both human and murine PKD1L3 and/or PKD2L1 proteins. In some embodiments, the chimeric proteins express domains, regions, or fragments of human and/or murine PKD1L3 and/or PKD2L1 in conjunction with non-human or non-murine homologous protein domains (e.g., *Xenopus*, zebrafish, *C. elegans*, for example). In some embodiments, the cells comprise a chimeric PKD1L3 and/or PKD2L1 proteins are used to study structure/function relationships, and other assays to characterize sour taste receptor activity and function.

In some embodiments, derivatives of human embryonic kidney 293T cells are used for optimal expression of human PKD1L3 and/or PKD2L1 proteins or fragments thereof at the cell membrane. In some embodiments, a derived human embryonic kidney 293T cell line is a Hana3A cell line configured to express, via stable or transient transfection, one or more of receptor transporting proteins (e.g., RTP1, RTP2), receptor expressing enhancer proteins (e.g., REEP1) (Behrens et al., 2006, J. Biol. Chem. 281:20650-20659; incorporated herein by reference in its entirety), and/or the olfactory neuron specific G-protein $G_{olf}$ protein (Jones & Reed, 1989, Science 244:790-795, incorporated herein by reference in its entirety). In some embodiments, a further derivation of the Hana3A cell line is the "44" cell line configured to express, via stable or transient transfection, one or more of brain synembrin (Ric8B), the heat shock protein 70 (HSP70) homolog HSC70T, and/or an RTP1A1 protein. For example, expression of human PKD1L3 and human PKD2L1 in the cell membrane of 44 cells expressing one or more of Ric8B, HSC70T and/or RTP1A1 is enhanced as compared to expression is Hana3A cells or 293T cells.

EXAMPLES

Example 1

In Situ Hybridizations

Procedures for non-radioactive hybridization were previously described (Saito et al., 2004, Cell 119:679-691). Briefly, digitonin (Dig) labeled RNA probes were hybridized, washed and detected by alkaline phosphatase conjugated anti-Dig antibodies followed by incubation with NBT/BCIP. For two-color fluorescent in situ hybridization, RNA probes were labeled with Dig or FITC (Roche). FITC labeled probes were detected by horse radish peroxidase (HRP) conjugated anti-FITC antibodies followed by TSA-Cy3 (Perkin-Elmer). HRP was inactivated by incubating with PBS containing 1% hydrogen peroxide for 30 min., and Dig labeled probes were detected by HRP conjugated anti-Dig followed by TSA-FITC.

Example 2

Immunoprecipitation

Protocols used for immunoprecipitation were previously described in Saito et al, 2004.

Example 3

Cell Surface Protein Expression

Protocols used for cell surface expression of proteins were previously described in Saito et al., 2004.

Example 4

Cell Culture, Gene Cloning and Calcium Imaging

Cell tissue culture was performed as previously described in Saito et al., 2004. The PKD1L3 gene (SEQ ID NO:1) was cloned into the mammalian expression vector pDisplay (Invitrogen), and the PKD2L1 gene (SEQ ID NO:5) was cloned into the mammalian expression vector pCI (Promega). For calcium imaging, pDisplay-PKD1L3 and/or pCI-PKD2L1 were transfected into cells (previously seeded on glass coverslips) using Lipofectamine 2000 (Invitrogen). Following incubation, the transfected cells were loaded with fluo-4 (Molecular Probes) and fura-red (Molecular Probes) for 45 min. at room temperature prior to analysis.

Results

The mouse genome contains at least 33 TRP channel members. To identify TRP ion channel members functioning in taste transduction, in suit hybridizations were performed using probes against all 33 TRP channel members (Corey et al., 2004, Nature 432:723-730) against sections of circumvallate papilla of the mouse taste tissue. Probes for TRPM5 labeled a subset of taste cells, and probes for PKD1L3 and PKD2L1 also hybridized to taste cells. A similar expression pattern was observed with rat circumvallate papilla. Other TRP channels did not show robust expression in taste cells.

In circumvallate papilla, around 20% of the taste cells expressed PKD1L3 and PKD2L1. To examine the expression of PKD1L3 and PKD2L1 in different taste areas, in situ hybridization with sections from circumvallate, foliate and fungiform papilla, and palate was performed. PKD2L1 expression was observed in a subset of taste cells in all four different taste areas, whereas PKD1L3 expression was only seen in circumvallate and foliate papillae. Additional in situ hybridization experiments did not reveal significant expression of other PKD family members in fungiform papilla or palate.

To investigate the correlation of TRPM5, PKD1L3 and PKD2L1 expression cells in taste buds, double-labeled fluorescent in situ hybridizations were performed. In circumvallate and foliate papilla, almost all of the PKD1L3 positive cells were also PKD2L1 positive, indicating these two molecules are expressed in the same cells. In contrast, TRPM5 signals did not co-localize with PKD2L1 or PKD1L3 indicating different taste cells express TRPM5 and PKD1L3/PKD2L1. In fungiform papilla and palate, PKD2L1 positive cells were PKD1L3 negative, confirming the absence of PKD1L3 expression in these two areas.

To examine mRNA expression of PKD1L3 and PKD2L1 in different tissues, RT-PCR was performed using mRNA for 16 different tissues including taste tissues (circumvallate and foliate papillae). Both PKD1L3 and PKD2L1 were abundantly expressed only in taste tissues and testis, whereas they were absent or only faintly expressed in all other tissues tested (GAPDH positive control RT-PCR showed expression in all tissues).

Taste reception occurs at the taste pore where the apical tip of each taste cell dendrite topped with microvilli is accumulated. To demonstrate the co-localization of PKD1L3 and PKD2L1 at the apical tip of the taste cell dendrite, antibodies against PKD2L1 were generated to analyze the PKD2L1 cellular localization within the taste cells. Immunostaining with rat and mouse circumvallate and foliate taste tissues demonstrate that PKD2L1 localized at the apical end of a subset of taste cells at the taste pore area, with weaker labeling throughout the positive cells. Preincubation of the antibody with peptide antigen (10 ng/ml) abolished the taste cell staining, thereby confirming the specificity of the antibody. Monoclonal IP3R-3 antibody marks PLCb2 and TRPM5 expressing bitter, sweet and umami sensing cells (Clapp et al., 2001; Miyoshi et al., 2001). Double staining using antibodies against PKD2L1 and IP3R-3 revealed different sets of taste cells were expressing PKD2L1 and IP3R-3, consistent with mRNA expression analysis. Therefore, the interaction between PKD1L3 and PKD2L1 is consistent with the role for PKD1L3 and PKD2L1 in taste reception.

Since Hanaoka et al. (2000) had previously suggested that the C-terminal cytoplasmic domains of related PKD 1 and PKD2 domains interacted and created functional channel expression, experiments were performed to investigate whether PKD1L3 and PKD2L1 also formed functional heteromeric receptors. Cell surface expression of PKD1L3 was investigated with and without the presence of PKD2L1. PKD1L3 was tagged with HA at the N-terminal extracellular domain. When PKD1L3 was expressed alone in HEK293T cells, no cell surface expression was observed when compared to control BFP signals (PKD1L3 was observed when the cells were permeabilized and stained demonstrating cytoplamic expression). It had been previously demonstrated by Murakami et al. (2005, J. Biol. Chem. 280:5626-5635) that PKD2L1 alone is not transported to the cell surface in heterologous cells. Therefore, interaction between the two molecules is necessary for their cell surface expression.

Bitter taste receptors (T2R5) and sweet and umami receptors (T1R5) are co-expressed with TRPM5, PLCb2 and IP3R-3 proteins. Since PKD1L3 and PKD2L1 positive cells do not co-localize with TRPM5 or IP3R-3 positive cells, it was tested whether these two proteins were involved in another taste sensation; such as sour or salty. To examine whether PKD1L3/PKD2L1 function as taste receptors, calcium imaging experiments were carried out using HEK293T cells transiently expressing PKD1L3 and/or PKD2L1. The cells were transfected with expression vectors encoding PKD1L3 and/or PKD2L1, loaded with calcium sensitive dyes (fluo-4 and fura-red), and stimulated with various taste chemicals and osmolarity solutions. When calcium concentration inside the cell is upregulated upon stimulation with ligands, the fluo-4 signal increases whereas the fura-red signal decreases, thereby allowing ratiometric measurements of intracellular calcium concentration (Wong et al., 2002, Nat. Neurosci. 5:1302-1308). It was demonstrated that cells expressing both PKD1L3 and PKD2L1 responded to solutions containing citric acid (25 mM, pH 2.6), whereas cells expressing either PKD1L3 or PKD2L1, or neither of them, showed little or no calcium response when treated with citric acid. When extracellular calcium ions were eliminated from the bath solution, the calcium response from citric acid was abolished, demonstrating that calcium ionw were coming from the extracellular solution. The experiments demonstrate that PKD1L3 and PKD2L1 form functional channels that are activated by citric acid. Citric acid elicits a more sour response at the same pH when compared to hydrochloric acid. Consistent to this notion, hydrochloric acid at the same pH caused much less of a calcium response in cells expressing both proteins. Further, function of the two protein heteromer was not inhibited by the ASIC inhibitor amiloride or the HCN inhibitor Cs+. Additionally, PKD1L3/PKD2L1 did not respond to salt (NaCl), bitter chemicals (quinine, cyclohexamide, PROP), sucrose, saccharin, or the umami compounds I-glutamate and IMP. Therefore, heteromers of PKD1L3 and PKD2L1 function as sour taste receptors.

PKD1L3 has homology to PKD1; both have a large extracellular domain followed by eleven transmembrane domains, whereas PKD2L1 is similar to PKD2; both have six transmembrane domains like most of the TRP channel members. PKD1 does not appear to function as an ion-conducting channel, but rather plays a role in sensing mechanical flow, whereas PKD2 forms a functional ion-conducting channel (Gonzalez-Perrett et al., 2001, Proc. Natl. Acad. Sci. 98:1182-1187; Nauli et al., 2003, Nat. Genet. 33:129-137). Chen et al. (1999) showed that PKD2L1 was capable of forming a functional calcium permeable channel, whereas it was not known whether PKD1L3 alone could form an ion-conducting channel. Calcium imaging experiments found that acid stimulation (e.g., citric, hydrochloric, maleic) opens calcium permeable channels. The present invention is not limited to a particular mechanism. Indeed, an understanding of the mechanism is not necessary to practice the present invention. Nonetheless, it is contemplated that PKD1L3 functions as a sour sensing receptor and PKD2L1 functions as an ion-conducting channel. An additional possibility is contemplated, in that PKD2L1 functions as a sour receptor and PKD3L1 functions as a facilitator of PKD2L1 expression.

Sour sensation is not a simple measurement of pH in a solution. For example, at the same pH, citric acid or acetic acid tastes more sour than hydrochloric acid (Ganzevles and Kroeze, 1987, Physiol. Behay. 40:641-646; Makhlouf and Bum, 1972, Gastroenterology 63:67-75). Similarly, calcium imaging experiments using mouse taste tissue slices showed that citric acid is a more potent sour ligand than hydrochloric acid at the same pH (Richter et al., 2003). The present invention is not limited to a particular mechanism. Indeed, an understanding of the mechanism is not necessary to practice the present invention. Nonetheless, it is contemplated that sour taste receptors do not function as mere acid pH sensors. The experiments presented herein demonstrate that citric acid is more potent than hydrochloric acid in activating PKD1L3/PKD2L1 heteromers at the same pH. It is contemplated that citrate ions or an undissolved form of citric acid interacts with PKD1L3 and/or PKD2L1 and enhances the sensitivity of the hydrogen activated receptor. A similar mechanism can be found in umami taste sensations, where some nucleotides such as IMP potentiate the activation of the umami receptor T1R1/T1R3 to 1-amino acids (Li et al., 2002; Nelson et al., 2002).

It is not well understood why both PKD1L3 and PKD2L1 are needed for cell surface expression. The present invention is not limited to a particular mechanism. Indeed, an understanding of the mechanism is not necessary to practice the present invention. Nonetheless, it is contemplated that as the C-terminal cytoplasmic domain of PKD2L1 contains endoplasmic reticulum (ER) retention signals (Murakami et al., 2005), the C-terminal cytoplasmic domain of PKD1L3 also contains ER retention signals and the interactions between PKD2L1 and PKD1L3 mask these signals, thereby allowing the complex to be transported to the cell surface.

Previous studies have shown that different taste cells are responsible for sensing bitter, sweet or umami taste. It is demonstrated herein that PKD1L3/PKD2L1 expressing cells are segregated from TRPM5 and IP3R-3 expressing bitter, sweet or umami taste cells, thereby demonstrating that a subset of cells are sour sensing cells. Additionally, Caicedo et al. (2002, J. Physiol. 544:501-509; Richter et al., 2003) have shown that 23-25% of taste cells are activated by citric acid with calcium imaging of taste bud slices. This correlated with the present findings that approximately 20% of taste cells express PKD1L3 and PKD2L1.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for identifying a sour-taste receptor ligand, comprising:
   a) providing
      i) a sample comprising a sour taste receptor wherein said functional sour-taste receptor comprises two or more polycystic kidney disease (PKD) proteins, wherein said two or more PKD proteins include polycystic kidney disease 1L3 (PKD1L3) and polycystic kidney disease 2L1 (PKD2L1), and
      ii) a test compound;
   b) exposing said test compound to said sample; and
   c) measuring the activity of said sour-taste receptor in said sample in response to said test compound.

2. The method of claim 1, wherein said sample is a cell line.

3. The method of claim 1, wherein said cell line is a 293T cell line.

4. The method of claim 1, wherein said PKD1L3 and PKD2L1 are either human or murine.

5. The method of claim 1, wherein said test compound is from a list consisting of a naturally occurring molecule, a synthetically derived molecule, or a recombinantly derived molecule.

6. The method of claim 1, further comprising a reporting agent.

7. The method of claim 6, further comprising the step of d) detecting the presence or absence of a sour-taste receptor ligand based upon said reporting agent activity.

8. The method of claim 6, wherein said reporting agent is a fluorophore.

9. The method of claim 8, wherein said fluorophore is from a group consisting of fluo-4 and fura-red.

* * * * *